United States Patent
Sutter

(10) Patent No.: US 6,332,777 B1
(45) Date of Patent: Dec. 25, 2001

(54) DEVICE FOR FORMING A DENTAL PROSTHESIS

(75) Inventor: Franz Sutter, Bennwilerstrasse 42, CH-4435 Niederdorf (CH)

(73) Assignee: Franz Sutter, Niederdorf (CH)

( * ) Notice: Subject to any disclaimer, the term of this patent is extended or adjusted under 35 U.S.C. 154(b) by 0 days.

(21) Appl. No.: 09/424,508

(22) PCT Filed: May 20, 1998

(86) PCT No.: PCT/EP98/02966

§ 371 Date: Mar. 9, 2000

§ 102(e) Date: Mar. 9, 2000

(87) PCT Pub. No.: WO98/52490

PCT Pub. Date: Nov. 26, 1998

(30) Foreign Application Priority Data

May 24, 1997 (CH) .................................................. 1220/97
May 24, 1997 (CH) .................................................. 1222/97

(51) Int. Cl.⁷ ............................................................ A61C 8/00
(52) U.S. Cl. ............................................ 433/173; 433/214
(58) Field of Search .................................. 433/173, 172, 433/174, 214, 213

(56) References Cited

U.S. PATENT DOCUMENTS

| | | | |
|---|---|---|---|
| 5,564,924 | * 10/1996 | Kwan ................... | 433/173 |
| 5,688,123 | * 11/1997 | Meiers et al. ......... | 433/173 |
| 5,695,335 | * 12/1997 | Haas et al. ........... | 433/173 |
| 5,829,981 | * 11/1998 | Ziegler ................. | 433/214 |

FOREIGN PATENT DOCUMENTS

| | | | |
|---|---|---|---|
| WO 96/29019A | * 9/1996 | (CH) . | |
| 44 15 670 | 11/1995 | (DE) . | |
| WO 97/28756 | 8/1997 | (WO) . | |

OTHER PUBLICATIONS

Andre Schroeder et al. "Oral Implantology", Thieme Medical Publishers, Inc. New York, 1996, pp. 206–211.

Schroeder et al., "Orale Implantologie", 2$^{nd}$ Edition, 1994, pp. 209–214.

* cited by examiner

Primary Examiner—Gene Mancene
Assistant Examiner—Melba Bumgarner
(74) Attorney, Agent, or Firm—Crowell & Moring LLP

(57) ABSTRACT

A device for forming a dental prosthesis includes a support and an element which can be attached thereto, such as an impression element. The support has an anchoring part for anchoring in a bone or a master model, a shoulder with an annular shoulder surface, and a head. The impression element has an elastically deformable fixing agent. When the device is assembled, the fixing agent jams and/or latches with the support, either externally on the support, on the side of the shoulder facing the anchoring part, or in an axial hole of the support. The element can be quickly detachably connected to the support by placing it on top of the support, and can be quickly separated from the support by moving the support away. When the device is assembled, the support and the element can lay on top of each other with annular surfaces. The annular surfaces have fully circular outer edges which are visible from the outside in an approximately radial viewing direction.

28 Claims, 16 Drawing Sheets

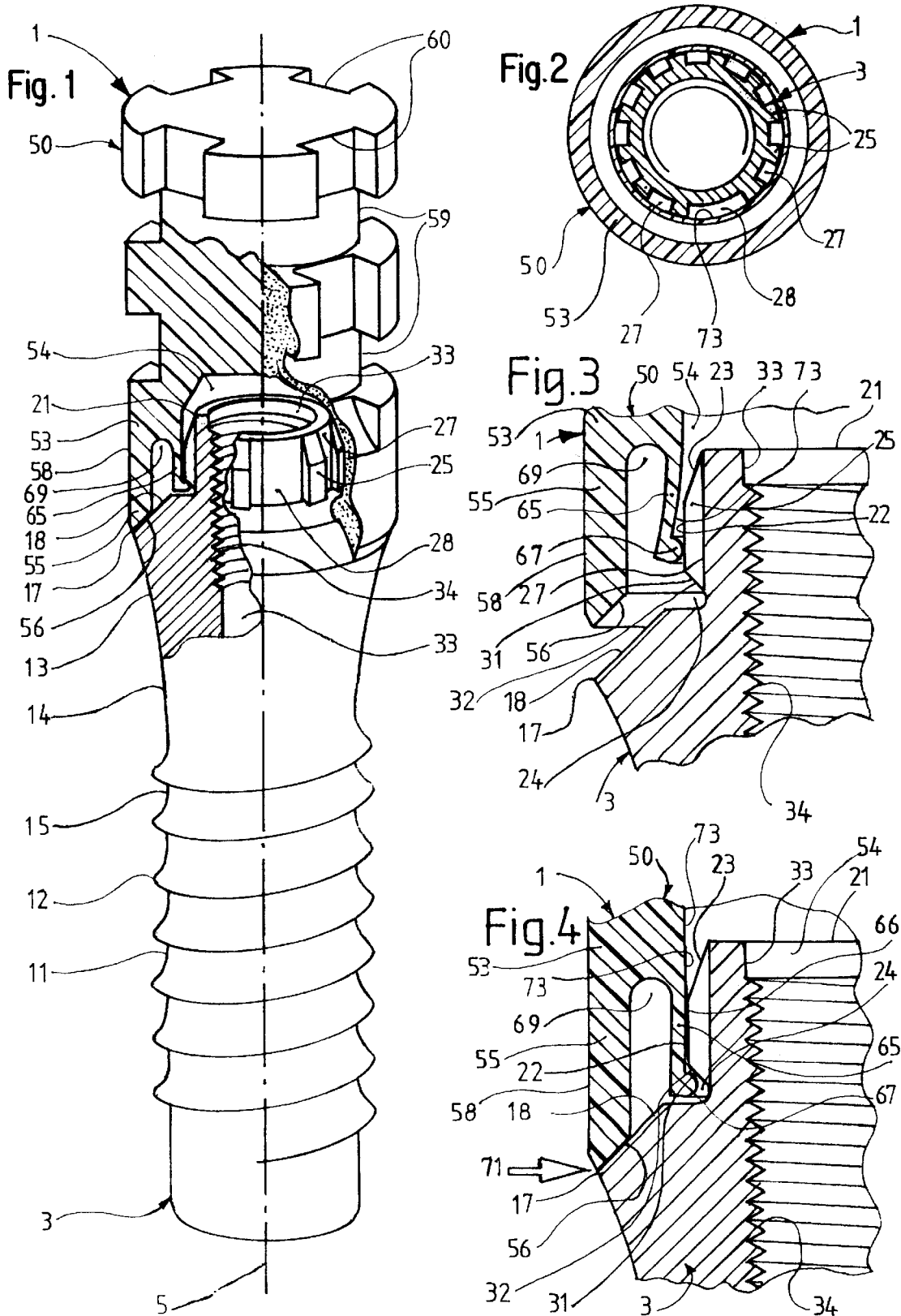

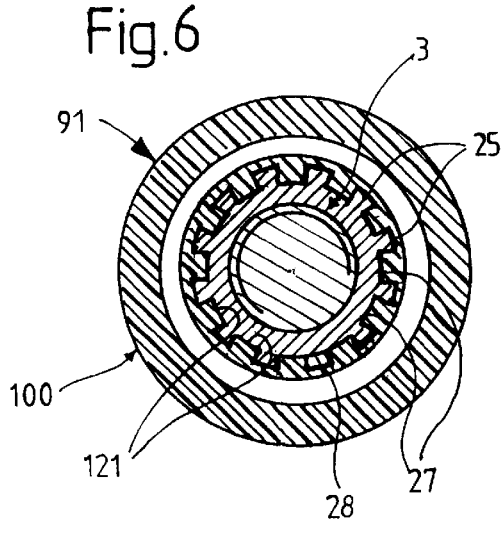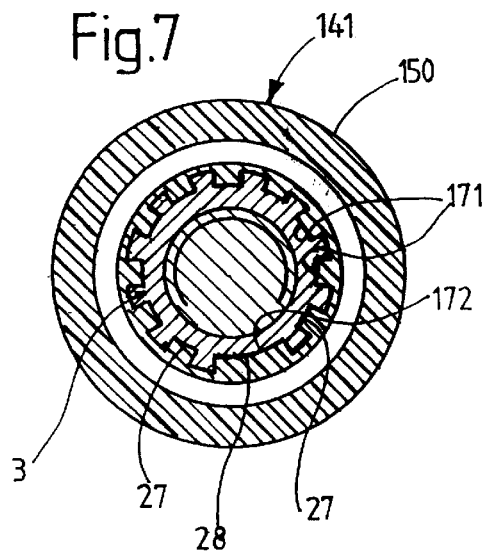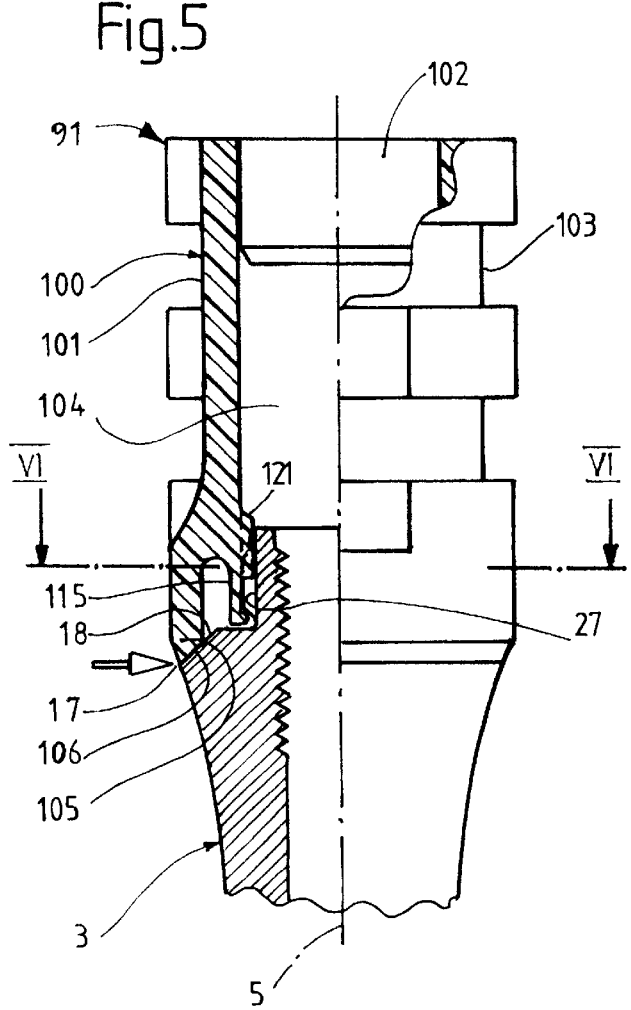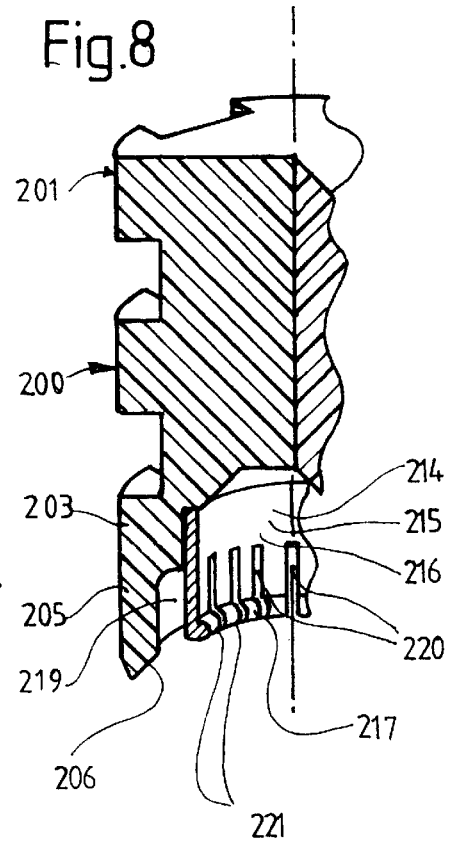

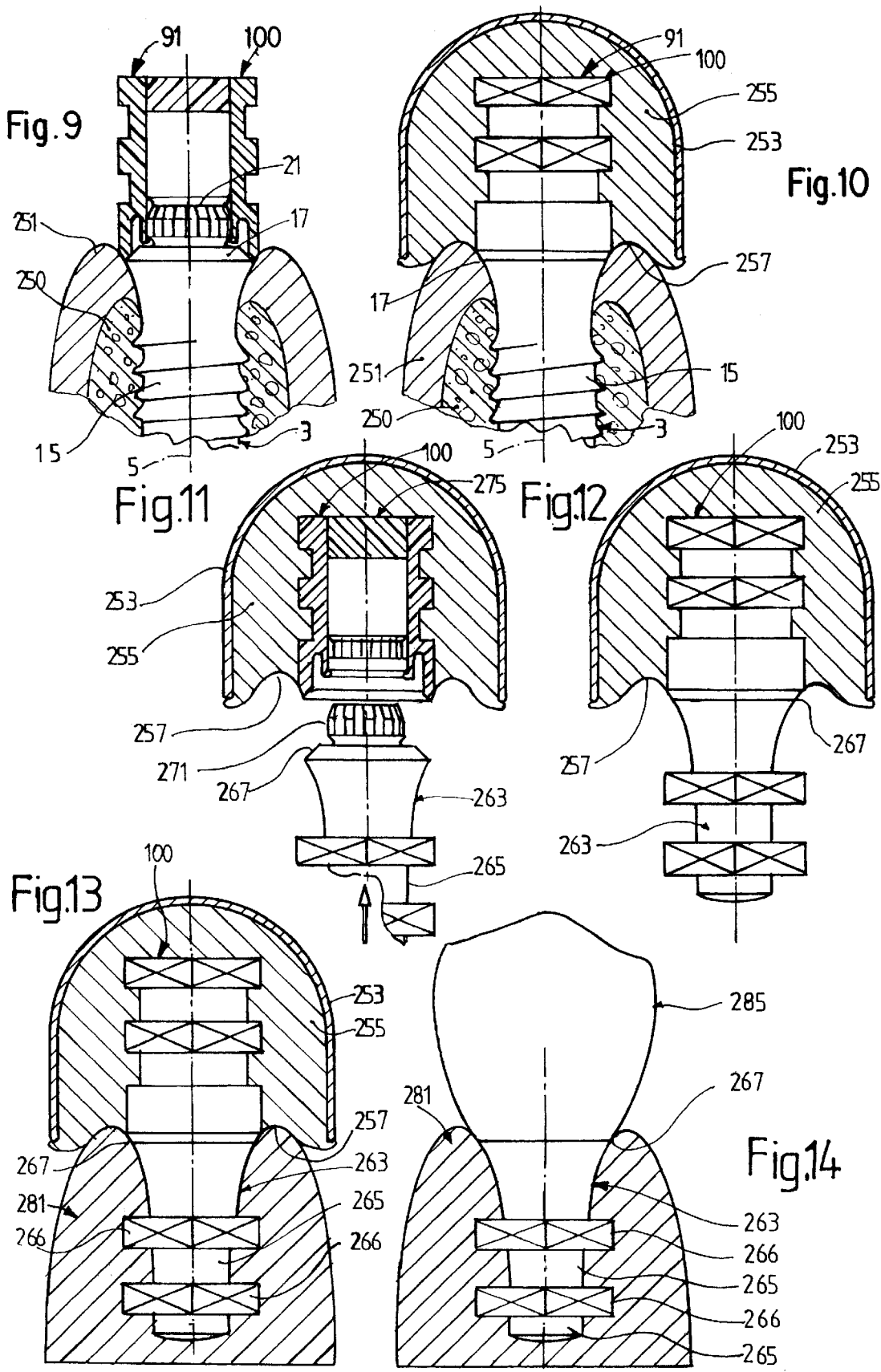

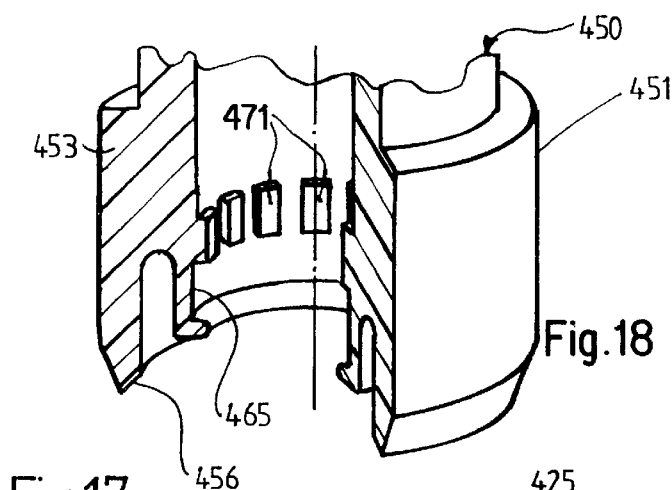
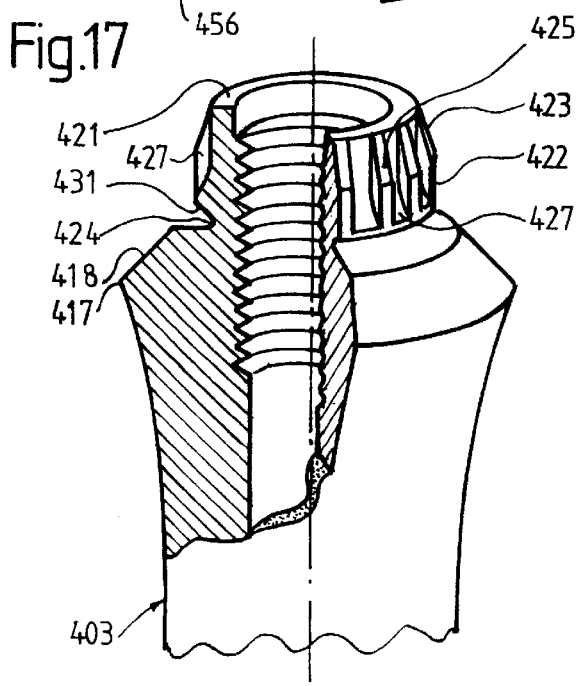
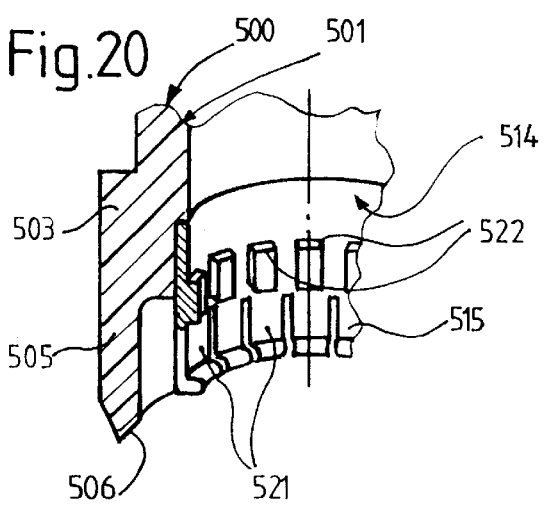
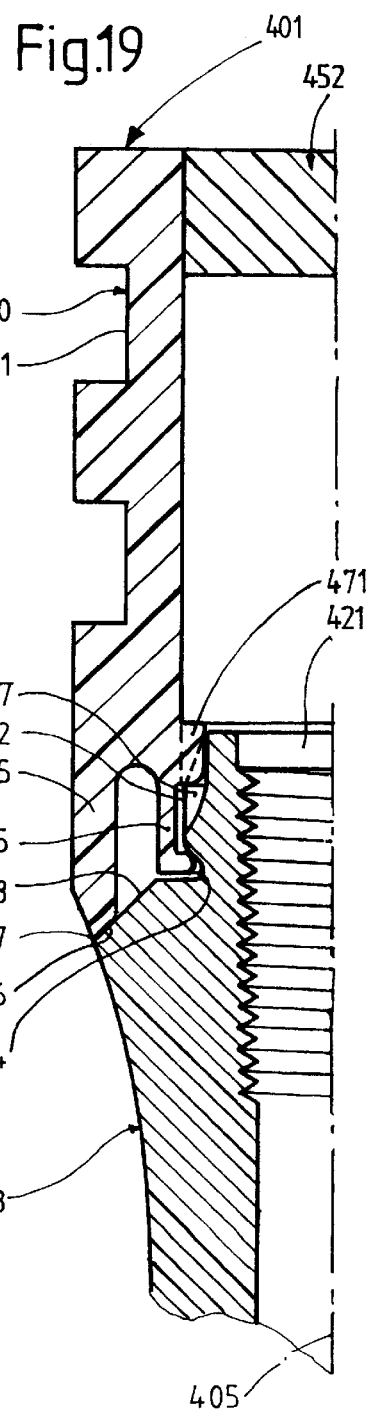

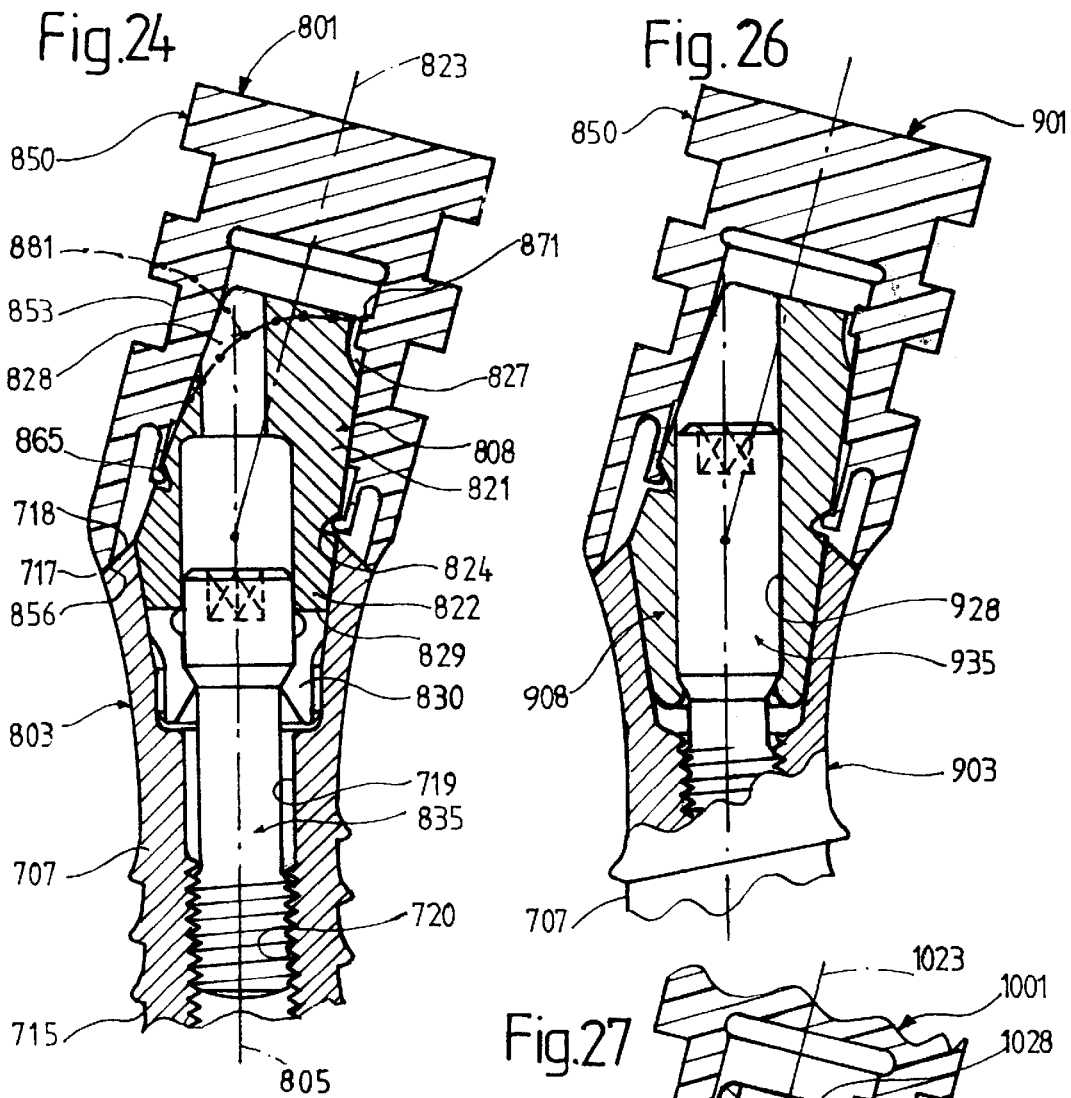
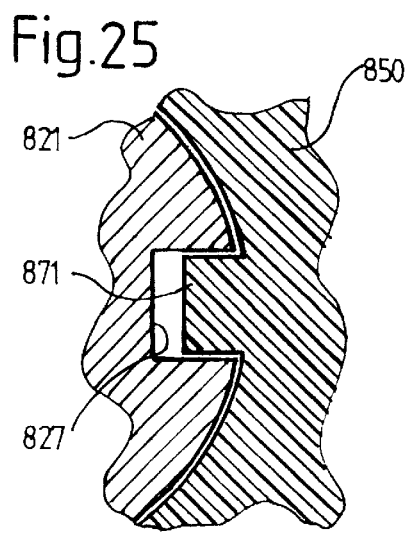
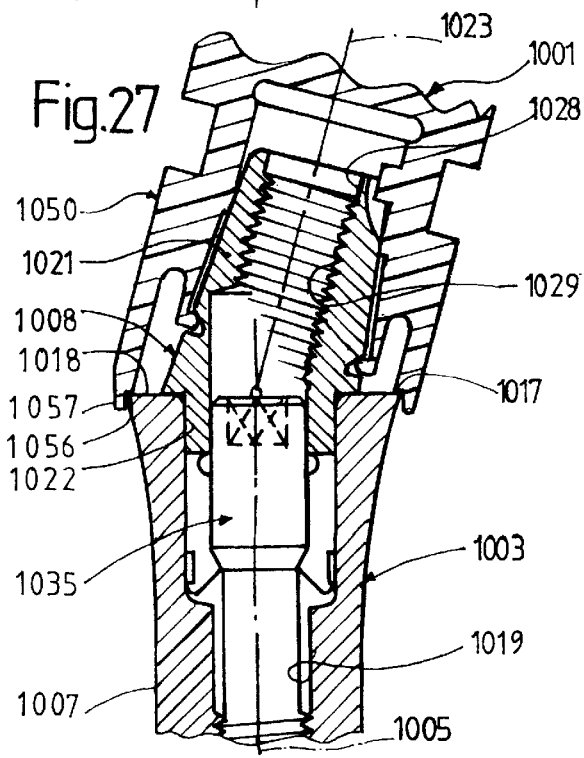

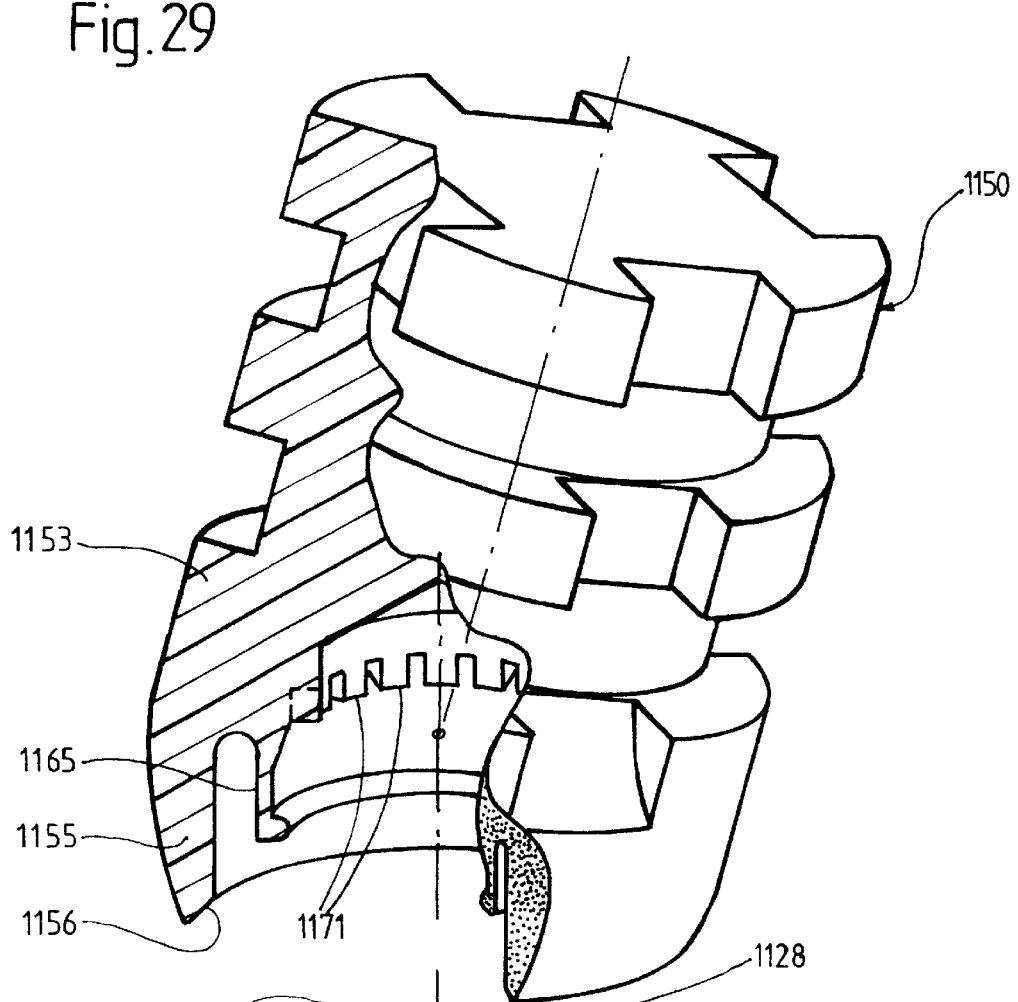
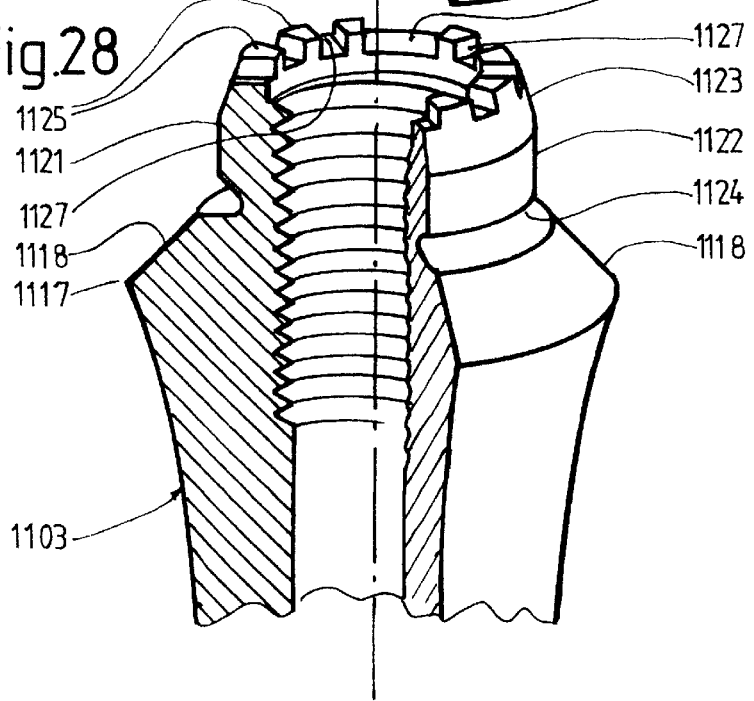

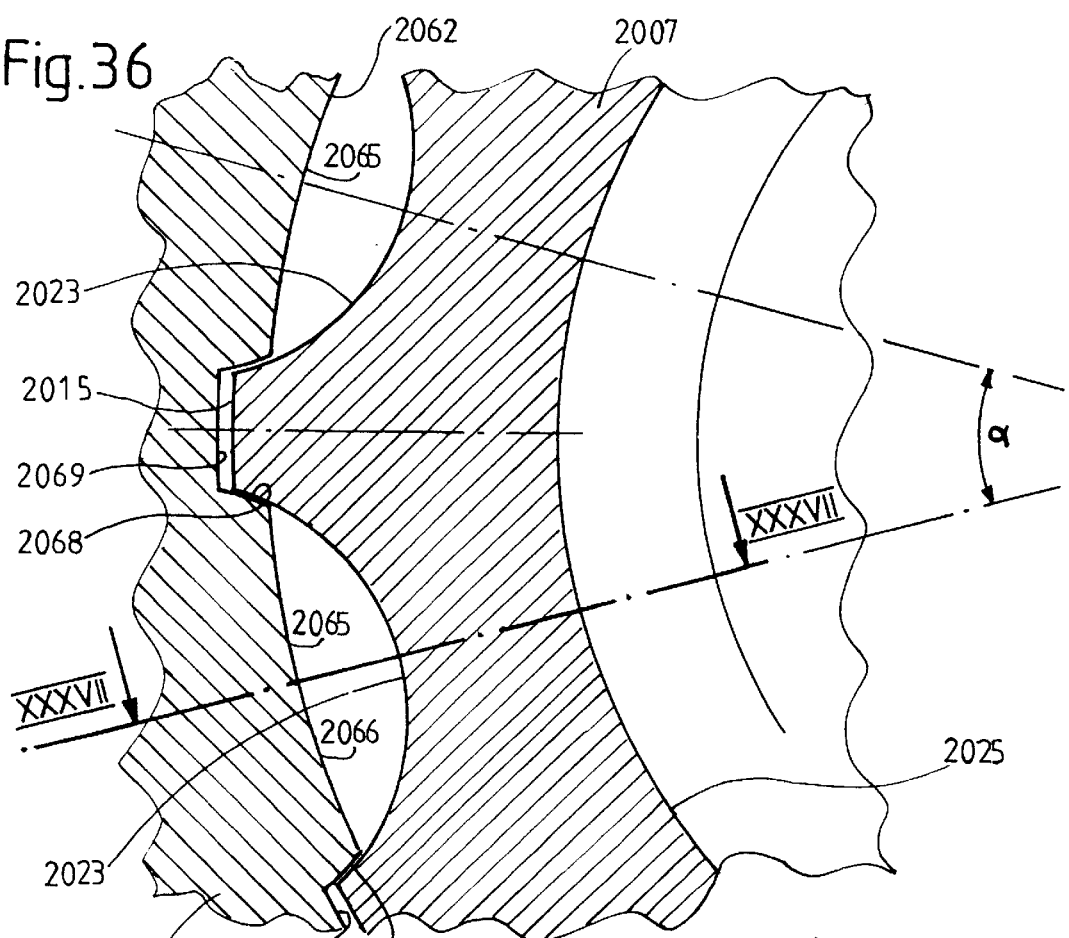
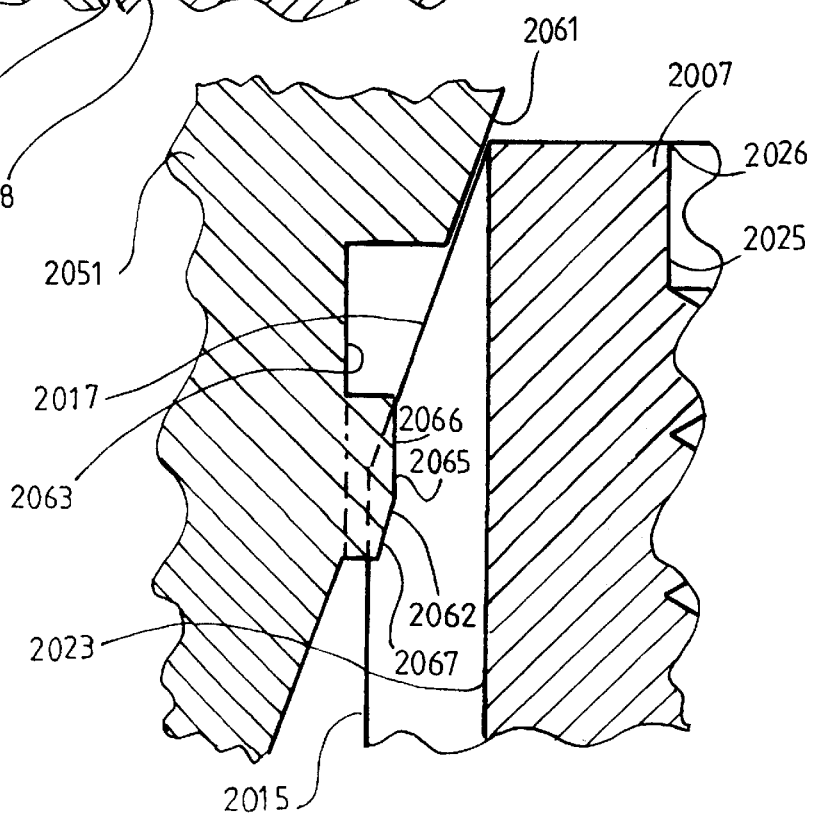

DEVICE FOR FORMING A DENTAL PROSTHESIS

TECHNICAL FIELD

The invention relates to a device for forming a dental prosthesis having a support and having an element which can be detachably connected using fixing means, where the support has an anchoring part designed to anchor in a bone and/or master model, a head designed to protrude from the bone or master model, and a shoulder present between this and the anchoring part. The dental prosthesis can involve a single false tooth, a bridge or a prosthesis forming several teeth. For example, the support can comprise a one-piece body or an implant and a secondary part, originally separate, which is fixed to the implant. The element which can be fixed on the support can, for example, comprise an impression element. This is also often called an impression cap or molding cap and, with the aid of an impression tray and impression material held by this and plastically shapeable for at least a certain period, is used to make an impression or a mold of the soft tissue surrounding the, or at least one, support in the mouth of a patient and/or perhaps of the bone as well as, if need be, of all natural teeth present near the support and then to produce a master model whose surface corresponds to the impression or mold.

The element which can be affixed to the support can, however, also be a healing element or a healing cap or a structural element and/or a superstructure which, for example, forms a crown and/or a bridge or a prosthesis having several artificial teeth.

STATE OF THE ART

A known device from the book "Oral Implantology", André Schroeder, Franz Sutter, Daniel Buser and Gisbert Krekeler, $2^{nd}$ edition, 1994 (edition in German) or 1996 (edition in English), Georg Thieme Publishing House, Stuttgart/New York, pages 209–214 (edition in German) or 207–210 (edition in English), has a support with an implant as well as a secondary part and an impression cap. The impression cap is temporarily affixed for the taking of the impression to the secondary part of the support using a screw. This known device has the disadvantage that it is often difficult, time consuming and unpleasant for the patient to first screw the impression cap fast to the support in the patient's mouth and after the impression to unscrew it again. Furthermore, before the taking of the impression, the impression tray must be provided with a hole for the or each support appropriate for the individual situation of a patient so that after the impression the screw which is screwed into the support can be unscrewed from the support and removed through the hole in the impression tray.

A known impression cap from DE 44 15 670 A has springable latch brackets at the edge which surrounds the opening to its interior. Since the latch brackets are located outside on the end designated for attachment with the support, the known impression cap is not suited for taking the impression of the shoulder of the support and the support's surroundings.

The known detachable connection of the healing element using screws and the known attachment of structural elements for forming crowns, bridges or prostheses with several teeth and/or a superstructure using screwing means of attachment is likewise often difficult and time consuming.

SUMMARY OF THE INVENTION

It is the object of the invention to do away with disadvantages of the known devices and in particular to make a device whose impression element or other element can quickly and easily be attached to a support protruding from either a bone or a master model and again detached from the support, where the element in its attached state should lie against the shoulder of the support tightly and with as small a gap as possible. In addition, it should be possible that the section, resting on the shoulder of the support, of the element attachable to the support be provided with a fully circular outer edge. Furthermore, the fixing means should avoid covering the shoulder so that the surfaces on which the support and the element touch each other preferably can be visible along the total circumference of the shoulder from the outside in an approximately radial viewing direction. If the element is designed as an impression element, an impression of the shoulder and its surroundings along the whole circumference of the shoulder should particularly be made possible.

This object is achieved according to the invention by a device for forming a dental prosthesis having a support and an element which is detachably connected to it by fixing means, where the support has an anchoring part for anchoring in a bone and/or master model, a head for protruding from the bone or master model, and a shoulder present between this and the anchoring part, where, when the device is assembled, the element lies on the shoulder with a supporting surface and, in a cross section, surrounds the head, and where the device is characterized in that the fixing means and/or the support are at least in places elastically deformable and that, when the device is assembled, the fixing means jam and/or latch with the support, either externally on the support on the opposite side of the shoulder from the anchoring part or in an axial hole of the support.

Advantageous further developments of the inventive subject matter follow from the dependent claims.

The element which is attachable to the support comprises, for example, an impression element. The support and the impression element can, for example, be generally straight, so that the anchoring part and the head of the support as well as the impression element are coaxial and generally rotationally symmetric with respect to a axis of symmetry of the support. The head of the support and/or the impression element, however, can be at an angle with respect to the anchoring part of the support and the part forming its shoulder and can define an axis which forms an angle with the axis defined by the anchoring part and the shoulder of the support, which angle is preferably no more than 30° and, for example, is around 10° to 20°.

In an advantageous embodiment of the inventive object, the fixing means in at least one region under elastic deformation are bendable and/or stretchable and/or can be pressed together. The support is preferably made of a metallic material and is preferably for the most part essentially stiff and rigid but can possibly have a fixing section onto which the fixing means grip and which is formed and sized such that the fixing section is elastically deformable, that is, having resilient form, and is more or less spring-like.

The device according to the invention makes it possible with a straight support as well as a support with a head at an angle for the impression element or other element to be connected with it—by sticking it on the support by jamming and/or clipping and/or latching—so as to be quickly detachable and afterwards to be detached again from the support by pulling away without necessitating a screw's being screwed in and later screwed out again.

When the element is held on the support, the fixing means cause, in an appropriate embodiment, a force which presses the impression element against the shoulder of the support. Thus it can be ensured that the element lies against the shoulder of the support at least nearly without a gap.

At the shoulder, the support preferably has an annular shoulder surface. The impression element or other element preferably has an annular supporting surface. The shoulder surface of the support and the supporting surface of the element are, for example, both conical or both flat and preferably, when the device is assembled, lie against each other out to their outer edges. The support and the element are further advantageously designed such that the outer edges of the shoulder surface and of the supporting surface are fully circular and, when the device is assembled, are visible along their whole circumference from the surroundings of the device in viewing directions which are approximately radial and at a right angle to the axis of the anchoring part and the shoulder of the support.

The impression element preferably has a rigid wall which delineates an interior space. The preferably elastically deformable fixing means are then preferably located completely in the interior of the impression element so that the fixing means cannot come into contact with the impression material which surrounds the impression element while the impression is being made. Thus, the fixing means, which moves somewhat during the connection of the element to the support and also during the detachment of the element from the support, are prevented from bringing pressure to bear on the impression material, which is plastically deformable at least for a certain period, something which could influence the precision of the impression.

Bridges, partial prostheses, and total prostheses are often attached with two or possibly even more supports. The supports, and particularly their heads, then ideally have axes which are parallel to each other. In reality, however, the axes are frequently at an angle with respect to each other and, for example, convergent or divergent to the free ends of the heads. The devices in accordance with the invention are designed in an advantageous embodiment such that an impression element can also be put onto the head and pulled off it in a direction of movement which is inclined with respect to the axis of a head. One can then simultaneously pull two or more impression elements which are held on the supports and embedded in impression material off of the supports when the axes of the support heads are at an angle to each other and form angles which are, for example, as great as 30° or even 40°. When being detached from the support and connected with it, the impression element and its fixing means can be moved, for example, in a direction over the heads which forms an angle as great as 15° or even 20° with the axis of each support head.

In an advantageous embodiment of the device, the shoulder has a shoulder surface which is conical and tapers towards the free end of the head, and the head has a head section which is essentially parallel to the axis and generally cylindrical and has as well a head section which tapers from this towards the free end of the head and is generally conical and makes a conical surface which forms a smaller angle with the axis than the conical shoulder surface. In addition, the impression element preferably has a supporting surface, which lies without a gap on the conical shoulder surface when the device is assembled, and a conical inner surface which is supported by the conical head section with little play. The play mentioned between the conical head section and the cap can be, at least in certain directions, at most 0.02 mm or only 0.01 mm at most, preferably can lie in the range of micrometers and, for example, can be at most 5 $\mu$m or at most 3 $\mu$m.

The axial measurement of the height of the head is advantageously so small that the support can be inserted into a patient's mouth as desired either subgingivally, transgingivally, or in the position half sunk in the gingiva ("semi-submerged").

In an advantageous embodiment of the device, the head of the support has at least one positioning recess located on at least one outer surface of the head, for example on the circumferential surface and/or on the front surface. When the fixing means engage with a fixing section of the support located on the support exterior, the or each positioning recess is located preferably on the opposite side of a fixing surface from the anchoring part, with which fixing surface the fixing means engage, and comprises, for example, an approximately axial or approximately radial or inclined groove or notch. The head and the anchoring part of the support are, for example, coaxial as well as generally rotationally symmetric with respect to an axis of symmetry of the support. The head can then, for instance, have a positioning section with several positioning projections and positioning recesses or positioning spaces which alternately follow one after the other around the axis of the support. The recesses then include, for instance, several first recesses with the same shapes, as well as the same measurements, and a second recess, which has a larger measurement in at least one direction than the first recesses. The second recess is, for example, wider and/or deeper than the first recesses. The first recesses, which are next to each other, then are at measured, equal distances from each other along a partial circle which is coaxial with the axis of the support and together define a circle division, or, put briefly, a division. For further clarification, let it also be noted that the division is equal to the $n^{th}$ part of a full circle, where n is a whole number and advantageously is at least 6 and not higher than 72, so that the division angle lies within the range of 60° to 5°. The second recess can, for instance, be formed, at least conceptually, by one's starting off with identical projections, distributed evenly around a full circle, and first recesses and then removing or leaving off one or possibly more of these projections. A second, broader recess can, however, instead be formed by making one projection or two neighboring projections narrower than the other projections.

The impression element can have at least one positioning projection which engages with the or a positioning recess of the support and thus defines a rotation position of the element with respect to an axis of the support and ensures that the element will not turn around the axis of the support. If the support has several equally formed first recesses and a deeper and/or wider second recess, the element can, for instance, have a positioning section with positioning projections distributed evenly along its circumference, which projections are separated from each other by recesses or spaces, and are as well all formed the same and can all be engaged with all positioning recesses of the support. This kind of element can be attached to the support in different, selectable positions, that is rotation positions, with respect to the axis of the support, where each selectable position, that is rotation position, is defined by the projections and recesses of the element and support which engage with each other and where the angle of rotation between the neighboring rotation positions is equal to the division angle determined by the division mentioned. This method of attachment of an element to the support is referred to in the following as multi-positioning of the element.

If the support only has one single positioning recess, the impression element can have a positioning projection which fits in this recess. If the support has several first positioning recesses and a second positioning recess, the element can, for instance, have a positioning section with several identical positioning projections which fit into the first recesses of the support as well as with a positioning projection which is wider and/or higher and which fits into the second recess of the support but cannot be engaged with the first recesses of the support. In these versions the element can only be connected to the support in one single rotation position with respect to the support's axis. These methods of attachment of an element to the support is referred to in the following as uni-positioning of the element.

The impression element can, however, also be produced without a positioning section and, in particular, without positioning projections and can be designed such that it does not engage with any positioning recess of the support after attachment to the support. The element can then be connected to the support in any rotation positions. This is referred to in the following as free-positioning of the element.

In an advantageous design of the support, one can thus by choosing in this manner jam on and/or clip on an impression element or other element by multi-positioning, or an element by uni-positioning or an element by free-positioning. Which type of element best serves depends on the type of dental prosthesis to be made and the individual medical indication.

As already mentioned, the element which is attachable to the support can also comprise a healing element or a healing cap or a structural element and/or a superstructure which serves to form a crown or a bridge or a prosthesis having several false teeth. Many characteristics and advantages referring to impression elements described previously and subsequently likewise apply to healing elements, structural elements and superstructures.

BRIEF DESCRIPTION OF THE DRAWINGS

The inventive object and further advantages of it are explained following using the exemplary embodiments shown in the drawings. The drawings show FIG. 1 a device, represented partially in projection at an angle and partially in cross section, having a one-piece support, and an impression element attached to it, FIG. 2 a cross section of the head of the support and the impression element designed for free-positioning, FIG. 3 an axial cross section through sections of the support and the impression element during the putting of the latter onto the support, FIG. 4 an axial cross section though the parts seen in FIG. 3 when the device is assembled, FIG. 5 a device shown partially in an axial cross section and partially in projection with an impression element for multi-positioning, FIG. 6 a cross section along the line VI—VI in FIG. 5 of the device shown in this, FIG. 7 a cross section of a device with an impression element for uni-positioning, FIG. 8 a projection at an angle of a different impression element which is cut away, the work steps FIGS. 9 through 14 during use of an impression element to form a structural element, FIG. 15 two devices shown partially in cross section, partially in projection with supports, inserted in a bone, and an impression tray, FIG. 16 parts from a device seen in FIG. 15 while the impression element is being removed from the support, FIG. 17 a projection at an angle of a different support which is cut away, FIG. 18 a projection at an angle of an impression element which is cut away and which goes with the support according to FIG. 17, FIG. 19 an axial cross section of a device with a support according to FIG. 17 and an impression element according to FIG. 18, FIG. 20 a projection at an angle of a different impression element which goes with the support according to FIG. 17, FIG. 21 an impression tray, an impression element designed according to FIG. 18, and a manipulation support, FIG. 22 an axial cross section of a device with a support in accordance with FIGS. 1 through 4, but with a different impression element, FIG. 32 a device, shown partially in an axial cross section, partially in projection, whose support comprises an implant and a straight secondary part, FIG. 24 an axial cross section of a device whose support has an implant and an inclined secondary part, FIG. 25 a cross section of parts of the device seen in FIG. 24 on a larger scale, FIG. 26 an axial cross section of a different device with an inclined secondary part, FIG. 27 an axial cross section yet another different device with an inclined secondary part, FIG. 28 a projection at an angle of a support whose head has positioning projections and recesses on its front side FIG. 29 a projection at an angle of an impression element which goes with the support in accordance with FIG. 28, FIG. 30 an axial cross section of a version of the device, FIG. 31 a projection at an angle of the head of the support seen in FIG. 30, FIG. 32 a detail of parts of the device according to FIG. 30, FIG. 33 an axial cross section of a version of a device, FIG. 34 a projection at an angle of a cut-open device with an implant, an impression element, and an attachment element, FIG. 35 an axial cross section of the device in accordance with FIG. 34, FIG. 36 a cross section of a region of the most recently mentioned device, taken from FIG. 34 along the line XXXVI—XXXI, FIG. 37 a detail from FIG. 35 on a larger scale, FIG. 38 a device with a healing cap, shown partially in an axial cross section, partially in projection, FIG. 39 an axial cross section of a device with an impression element, the FIGS. 40, 41 axial cross sections of parts of devices designed similarly to the device according to FIG. 39, FIG. 42 an axial cross section of a device with an impression element attached to the support.

DESCRIPTION OF PREFERRED WORKING EMBODIMENTS

Figure 15:
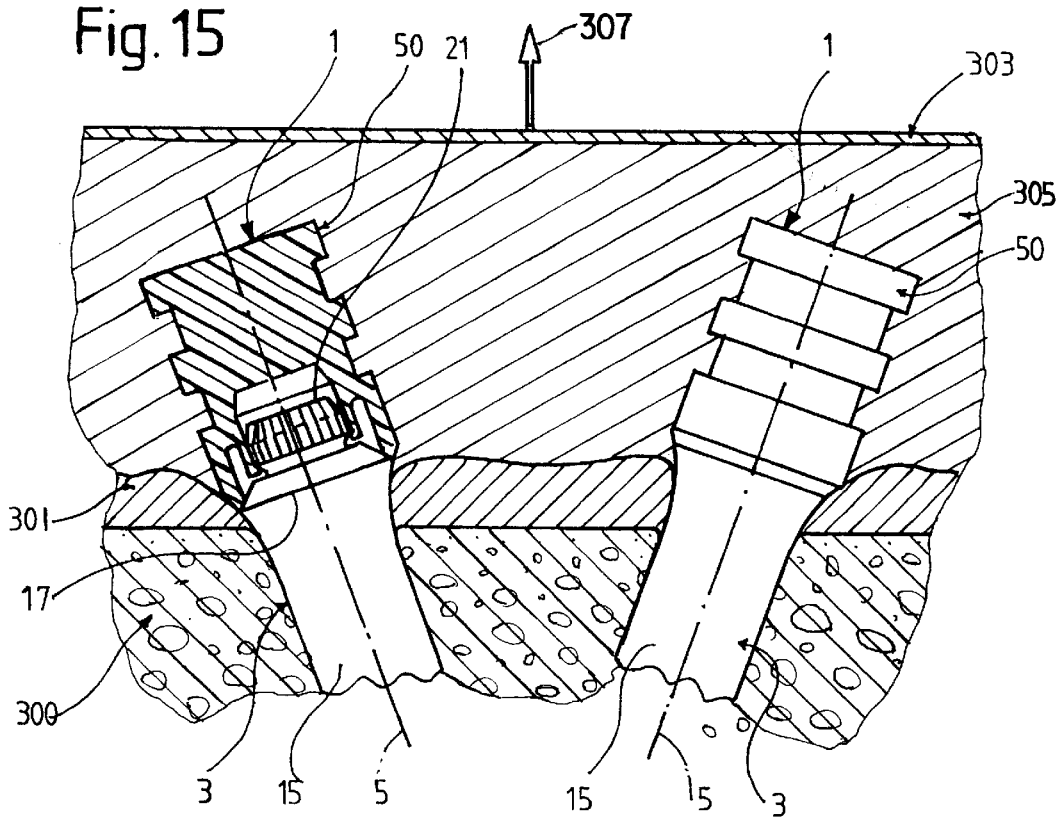

The device 1 seen in the FIGS. 1 through 4 has a support 3 comprising a one-piece implant. The support 3, or the implant, is longish and generally rotationally symmetric to an axis 5. The support 3 has a generally cylindrical section 11 with an outer threading 12 and a section 13 which is trumpet shaped, expanding away from the cylindrical section 11 in an upwards direction. The sections 11, 13 have a casing surface and/or outer surface 14. Together, the cylindrical section 11 and the lower end of the trumpet-shaped section 13 form the anchoring part 15 of the support 3. This, on the upper end of the trumpet-shaped section 13, has a shoulder 17 with an annular, conical shoulder surface 18, which is inclined from the anchoring part 13 towards the axis 5, forms an angle with it of 40° to 50°, for example 45°, and has a fully circular outer edge.

The support 3 has a narrow, annular, flat surface adjoining the upper inner edge of the conical shoulder surface 18 and has a head 21, which points upwards away from this and has a section 22 which is parallel to the axis and generally cylindrical and a conical section 23 which tapers upwards from this to the free end of the head. This forms an angle with the axis 5 which is smaller than the angle formed by the shoulder surface 18 and the axis 5 and preferably is 10° to 30°, approximately 15° to 25°, specifically, for example, about 20°. On its upper, free end, the head has a front surface which is annular, flat and forms a right angle with the axis. The cylindrical section 22 is separated from the upper end of the shoulder 17 by an annular groove 24. Both of the sections 22, 23 together form a positioning section and have positioning projections 25 and positioning recesses 27, 28 which alternately follow one after the other around the axis. There are present several identically-formed first positioning recesses 27 and a second, broader positioning recess 28. The latter can, for example, be designed by starting with twelve identical recesses, distributed evenly around a full circle and defining a division into $12^{ths}$, and with the projections placed between them and then leaving off or removing one of the projections, such that eleven equally formed projections 25 remain and ten first recesses. The recesses 27, 28 are formed by grooves and are parallel to the axis 5 and have, in particular, a floor which is parallel to the axis 5 and stretch from the lower end of the cylindrical section 22 to the upper, free end of the head 21, that is, up to its flat front face. The recesses 27, 28 are, for instance, a little bit shallower than the annular groove 24, where these depths are all measured from the circumferential surface of the cylindrical section 22. Furthermore, the radial distances of the deepest points of the recesses 27, 28 are approximately equal to the radius of the upper, thinner end of the conical section 23, such that, at the upper end of the conical section 23, the recesses 27, 28 approximately end at its edge.

The upper flank of the annular groove 24 forms a circular undercut 31 of the cylindrical section 22. Let it be noted that the undercut 31 is subdivided, due to the recesses 27, 28, into undercuts of the projections 27, which are separated from each other to a large extent and distributed around the axis 5, however, it is seen and referred to as one undercut. The undercut 31 serves as a fixing section and/or attachment section and at least essentially is formed from a fixing surface and/or attachment surface 32 which is inclined upwards and outwards away from the anchoring part 15 and is at least essentially conical. The surface, or more precisely its conical main part, forms an angle with the axis 5 which is at least 15°, at most 75°, and, for example, is approximately 40° to 50°. The projections 25 have tops, which are parallel to the axis 5 and formed by sections of the circumferential surface of the cylindrical section 22, tilted surfaces on their lower end which are formed by the undercut 31, and sloping surfaces on the upper end which are formed by the circumferential surface of the conical section 23. The floor of the annular groove 24 is curved in an axial cross section such that it smoothly and continuously connects the flat surface present on the upper end of the shoulder with the conical surface of the undercut 31.

The support 3 has a pocket hole 33, coaxial with the axis 5, which opens onto the front surface of the head 21 and has a section with an inner threading 34.

The device 1 further has an impression element 50. This is, at least for its lower part, hollow and cap shaped as well and has a rigid wall 53 which delineates an interior space 54 which opens to the bottom. The region of the impression element found above the interior space 54 has, for example then, a solid filled cross section. The lowest region of the wall 53, annular in its cross section, forms a supporting section 55 and has an annular, conical supporting surface 56 on its free end. Its outer edge is fully circular, forms the lowest point of the impression element, and adjoins the opening where the interior space 54 opens into the surroundings of the impression element 50. When the latter is connected to the support 3, the support surface 56 forms the same angle with the axis 5 as the shoulder surface 18 does and lies on at least one part of it, where both surfaces 18, 56 lie on each other, in particular out to their outer edges. The casing surface and/or outer surface 58 of the impression element has a section at the outer edge of the supporting surface 56 which touches the casing and/or outer surface 14 of the support and, moving upwards away from it, is inclined outwards in the same or a similar manner as the neighboring section of surface 14 of the support, so that both casing and/or outer surfaces 14 and 58 adjoin each other at the shoulder 17 seamlessly, continuously, and at least nearly smoothly and steadily. The short, inclined section of the casing and/or outer surface 58 then adjoins the generally cylindrical main section of the surface 58. This main section, however, has annular grooves 59 and axial grooves 60 which intersect each other, which provides the structure for the exterior form of the impression element.

The impression element 50 has means of attachment and/or fixing means 65, namely latching means 65, which are located completely inside the interior space 54 and are arranged above the supporting surface 56. The latching means 65 have a thin-walled, case-shaped section 66 which at its upper end is connected to the rigid wall 53 and in an undeformed state is roughly parallel to the axis 5 and is roughly cylindrical as well. Further, on the lower, free end of the case-shaped section 66, the latching means 65 have a nose 67 which protrudes inward and whose inner, free end is curved to be convex in an axial cross section. With the exception of their upper end which is connected to the wall 53, the latching means are separated from the supporting section 55 of the wall 53 by a annular space 69 which cuts into the impression element from its lower end. The latching means 65, along with the remaining parts of the impression element, comprise a one-piece body. This, for example, is made of a synthetic material which is thermoplastic, elastically deformable, however still relatively resistant to deformation and not of elastic. The case-shaped section 66 of the latching means does not have incisions or grooves and is uninterruptedly connected together for its whole axial length along its circumference, however it is so thin in measurement that it elastically deforms, in particular can be spread a little and can spring. When the impression element 50, originally separate from the support 3, is pushed onto the head 21 of the support in a direction which is approximately parallel to the axis 5, the nose 67 of the latching means 65 slides across the conical section 23 onto the cylindrical section 22 of the head 21. There the case-shaped section 66 is temporarily deformed from its cylindrical shape at rest and spread, as it is shown in FIG. 3. When the impression element reaches the position shown in FIGS. 1 and 4, the latching means snap behind or under the undercut 31 into the annular groove 24. The nose 67 then, with a surface section which is curved and inclines in an axial cross section, engages the inclined, conical fixing surface and/or attachment surface 32 of the undercut 31. The spring tension or initial tension of the latching means thus produces an axial force which presses the supporting surface 56 of the impression element 50 against the shoulder surface 18 of the support 3. This ensures that the two surfaces 18 and 56 lie upon each other, at least nearly, without a gap. In the upper regions of the support 3 and the impression element 50 which house them, the outer edges of the shoulder surface 18 and the supporting surface 56 form the outermost boundary of the support or impression element, respectively, and are not covered on the outside by any other parts of the device 1. Thus, the outer edges of the surfaces 18 and 56 are visible from the surroundings of device 1 along the whole circumference of said outer edges in a viewing direction which is approximately radial and perpendicular to axis 5 and which is indicated in FIG. 4 by an arrow. The interior surface 73 of the latching means 65 and of the section of the wall 53 which adjoins its upper end is, with the exception of the nose 67, essentially rotationally symmetric and smooth and, in particular, does not have any projection which engages with a positioning recess 27, 28. The impression element 50 can thus be attached to the support 3 in any rotation position and is freely positionable on the support, according to the terminology explained in the introduction.

The device 91 seen in FIGS. 5 and 6 has a support 3 which defines an axis 5 and is designed the same as the support depicted in FIGS. 1 through 4. The device 91 further has an impression element 100, generally hollow and cap-shaped. This comprises two parts which were originally separate and are made, for instance, of synthetic material, namely a case 101 with an axial hole through it and sealing element 102 which seals it on its upper end and is affixed to the case, for example by being pressed into the hole. Together with the sealing element 102, the outer cover of the case 101 forms a rigid wall 103. The region of the case's hole which is located under the sealing element 102 forms the interior space 104 of the impression element 100. The lowest section of the wall 103 forms a supporting section 105 with a supporting surface 106 which lies on the shoulder surface 18 of the support 3 when the device is assembled. The latching means 115 of the impression element 100 are in general designed similarly to those of the impression element 50 and make up a one-piece body together with the case 101 and, in particular, the supporting section formed by this.

The impression element 100 is, however, different from the impression element 50 in that, in the region where the fixing means and/or latching means 115 are connected to the rigid wall 103, the generally cylindrical interior surface of the case 101 has an annular positioning section with a wreath of positioning projections 121 pointing inward, between which there are positioning recesses. The projections 121 are all designed the same and define a division into $12^{ths}$. When the device 91 is assembled, one of the projections 121 protrudes into each first positioning recess 27 of the support, while two projections 121 engage with the second positioning recess 28. The positioning projections 25 of the support naturally then engage with positioning recesses of the impression element. The positioning projections 121 thus enable a multi-positioning of the impression element 110 in twelve different rotation positions, where the impression element then is assured against being turned when in any rotation position which can be chosen. In addition, the projections 121 engage only with the top sections of the recesses 27, 28, for instance at most with the top halves.

Moreover, the interlocking positioning projections and recesses of the support and the impression element have a certain play, for instance, in the radial direction. The impression element 100 can then, in spite of its positioning projections, be stuck onto the support in a direction of movement which forms a certain angle with the axis 5 of the support 3 and be pulled off of it.

The device 141 seen in FIG. 7 has a support 3 which is once again designed the same as the support depicted in FIGS. 1 through 4. The device 141 further has an impression element 150. This has ten first positioning projections 171 of the same design and a second, wider positioning projection 172. When the device 141 is assembled, each first projection 171 protrudes into first recess 27 of the support. Further, the second projection 172 protrudes into the second recess 28 of the support. The impression element 150 can therefore only be clipped onto the support in one single rotation position and is hence designed for the uni-positioning.

The impression element 200 seen in FIG. 8 has a one-piece cap 201, made of metallic material or synthetic material and having a rigid wall 203. Right at the bottom this has a supporting section 205 with a conical supporting surface 206. Above the supporting surface, the interior surface of the cap has first a wider and then a thinner cylindrical section. The fixing means and/or latching means 215 are formed by an annular and/or case-shaped insert 214, which is originally separate and made from metallic material or synthetic material, and possess a case-shaped, cylindrical section 216 whose upper part lies against the narrower cylindrical section of the interior surface of the cap, lines up with its upper end at an annular, radial, flat section of the interior surface of the cap, and is firmly connected with this by pressing on and/or gluing, for example. The fixing means and/or latching means 215 have a nose 217 which points inwards on their lower end. The lower section of the latching means 215 is separated from the supporting section 205 by an annular space 219 and subdivided into resilient tongues 221 by axial incisions 220 cut out from below.

Now, using FIGS. 9 through 14, the use is described of a support 3 and one of the previously described impression elements, for example the impression element 100. The bone 250 of a patient's lower jaw, shown schematically in cross section in FIGS. 9 and 10, is covered by soft tissue 251, that is by gingiva. A dentist makes a hole in the bone 250 and inserts the implant, which forms the support 3, into the hole such that the anchoring part 15 of the support is anchored in the bone, while the shoulder 17 and the head 21 protrude from the bone. The shoulder, for example, is located approximately at the level of the ridge of the soft tissue 251. When, after a certain length of time, the support has taken in the bone, the dentist puts, for instance, the impression element 100, designed for multi-positioning, onto the support 3. There the impression element 100 is detachably clipped onto the support 3 in the chosen rotation position and then, together with this, forms the device 91, already described using FIGS. 5 and 6. Now, in accordance with FIG. 10, the dentist presses an impression tray 253, filled with warm if necessary, soft, plastically deformable impression material 255, over the impression element 100 towards the soft tissue 251. The section of this surrounding the support 3, the parts of the device 91 which stick out of this, and possibly natural teeth which are still present in the vicinity of the support 3 then produce an impression in the impression material and are imprinted into this such that the impression material forms an impression surface 257. After the thickening and hardening of the impression material 255, the dentist lifts the impression tray and the impression element 100, which is embedded in the impression material, approximately parallel to axis 5 of the support, off of this, where the latching means of the impression element unlatch, and the latter is separated from the support. The tray 253, the impression material 255 therein, and the impression element 100 are now removed from the patient's mouth and taken to a dental technical laboratory, for example.

The manipulation support 263 seen in FIG. 11 comprises a one-piece manipulation implant, is generally rotationally symmetric with respect to an axis, and has an anchoring part 265, a shoulder 267, and a head 271 as well. The anchoring part 265 is different from that of the support 3 and also has some thick sections 266, which protrude outwards and form hexagonal rings or discs and serve to improve the anchoring. In contrast, the parts of the manipulation support located above the anchoring part and forming the shoulder and the head of the manipulation support are the same shape and size as that of the support 3 set in the bone 250. The head 271 of the manipulation support 263 is pushed into the interior space of the impression element 100 embedded in the impression material such that the latching means of the impression element latch behind the undercut of the head 271 and connect the impression element 100 according to FIG. 12 firmly but detachably to the manipulation support 263. This, together with the impression element 100, then forms a device 275. The impression element then lies with its conical supporting surface on the annular, conical shoulder surface of the manipulation support. After that, a pourable model material, or at least one that is easily plastically deformable, plaster for instance, is applied, for example poured and/or pressed, to the impression surface 257 around the anchoring part 265, and a master model 281, seen in FIG. 13, is formed from the model material, in which master model is anchored the section, protruding out of the impression material 255, of the manipulation support 263 and in particular its anchoring part 265. A dental technician or some other person now moves the tray 253, with the impression material 255 and the impression element 100, approximately parallel to the axis of the manipulation support 263 away from this and from the master model 281. There the latching means of the impression element unlatch. Then, a structural element 285, seen in FIG. 14, is detachably connected to the master model 281 and erected on it. The structural element 285 can have, for example, a metallic cap and a porcelain covering, be detachably affixed on the manipulation support with an occlusal screw, lie on the shoulder 267 with a supporting surface, and form a crown for a single false tooth. If the structural element 285 has the desired form, it is removed from the manipulation form, put in the mouth of the patient, and affixed to the support 3 with an occlusal screw, for instance, after which it lies on the shoulder 17 of the support 3 without any gaps.

The bone 300 of a patient's lower jaw, seen in FIG. 15, is covered by soft tissue 301 and provided with two holes in which the anchoring parts of two supports 3 are seen. These are tilted with respect to each other and diverge from the anchoring parts 15 to the heads 21, such that the axes 5 of both supports form an angle with each other of approximately 40°, for instance. An impression element 50 designed for free-positioning is clipped on each support 3, which impression element lies on shoulder 17 of the support and, together with it, comprises a device 1. After affixing the impression elements 50 on the supports 3, an impression tray 303 filled with impression material 305 is pressed against the soft tissue such that both impression elements 50 are embedded in the impression material. When the impression material has hardened, the dentist moves the impression tray 303, along with both the impression elements 50 imbedded in the impression material, away from the bone and the soft tissue in the direction indicated by the arrow 307.

Figure 16:
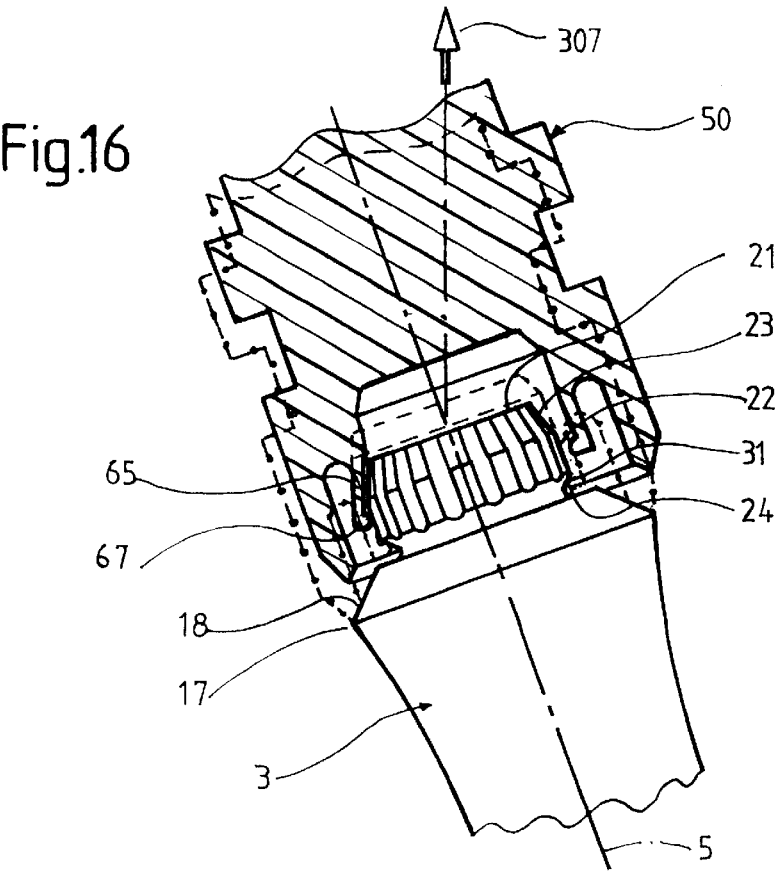

In FIG. 16, one of the impression elements 50 is shown with dotted lines when situated lying on shoulder 17 and shown with solid lines in a situation in which the cap 67 of the latching means 65 was unlatched from the annular groove 24 or undercut 31 of the support 3 and lies on the cylindrical section 22 of the support's 3 head 21. As one can see in FIG. 16, the resilient latching means become asymmetrically deformed there. The design described of the support's head 21 and the impression element's latching means 65, though, just makes it possible to remove two impression elements from the supports 3 both simultaneously and in the same direction when the axes of the latter form an angle of up to about 40° with each other. In addition, when the impression elements are removed from the supports, forces directed at the side come heavily to bear on the impression elements. These forces, it is true, cause the asymmetrical deformation of the flexible latching means mentioned, however, to a certain extent, only have an effect in the interior of the impression element so that they don't effect the exactness of the impression. The impression can then serve to form a master model, which aids, for example, in making a bridge or a partial or full prosthesis.

The device 401 seen in FIG. 19 has a support 403, depicted separately in FIG. 17, and an impression element 450, depicted separately in FIG. 18. Like support 3, the support 403 is made of a one-piece implant, defines an axis 405, and has a shoulder 417 with a conical shoulder surface 418 and a head 421 with a cylindrical section 422 and a conical section 423 as well. The head 421 is separated from the shoulder 417 by an annular groove 424 and has positioning projections 425 and positioning recesses 427 which alternately follow each other along its circumference. There are present, once again, several first recesses 427 of the same design and a broader second recess, not visible. The positioning recesses 427 run from the upper end of the head 421 along axial planes, however differ from the recesses of the support 3 in that, in an axial cross section, their floor is at least partially curved and in that they run out over the lower end of the cylindrical section 422 into its circumferential surface. The recesses 427 can, for example, be cut into the head with a disk milling cutter. On its upper side, the annular groove 424 forms an undercut 431 of the cylindrical section 422 of the head. The undercut 431 on this support is not subdivided by the recesses 427 and is made entirely of an uninterrupted annular surface and serves as a fixing and/or attachment section 431.

The impression element 450 comprises a case 451 and a sealing element 452, sealing its top, and has a rigid wall 453 with a supporting section 455 and also a conical supporting surface 456 and fixing means and/or latching means 465 which comprise a one-piece body together with the supporting section. The impression element 450 is, for example, designed for multi-positioning and has a wreath of identically designed positioning projections 471. These are sized such that they can engage into the upper end sections of the positioning recesses 427 of the support 403. The projections 471 have interior surfaces of which at least the lower sections are inclined towards the outside as they go down, for example.

The impression element 500, seen in FIG. 20, has a one-piece cap 501 with a rigid wall 503, which at the lower end forms a supporting section 505 with an annular, conical supporting surface 506. The impression element 500 further has an annular and/or case-shaped insert 514, located and attached in the same manner as the insert 214 of the impression element shown in FIG. 8, and fixing and/or latching means 515 having springable tongues 521. The insert 514, however, is different from the insert 214 in that, above the fixing and/or latching means, it also has a positioning section with a wreath of positioning projections 522 distributed along its circumference. These, for example, match the support 403 and are designed for multi-positioning.

Figure 21:
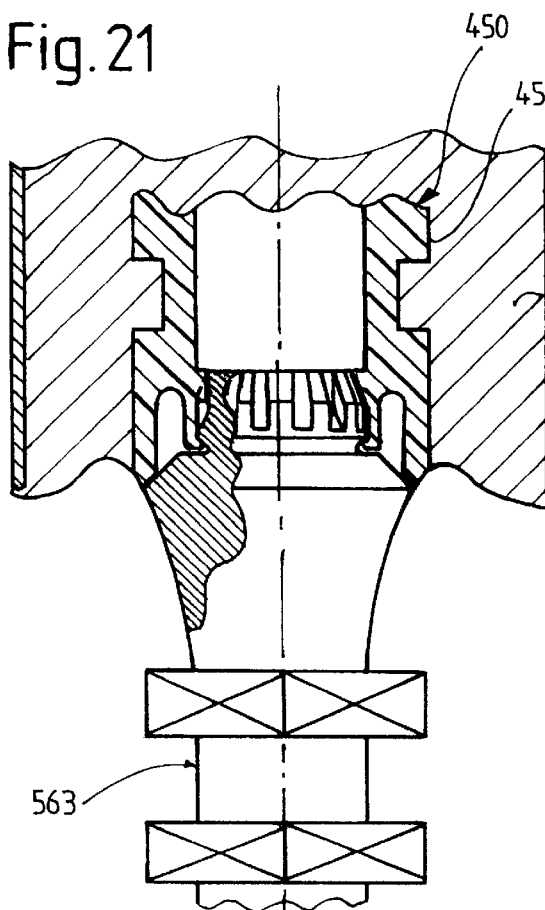

When the support 403 is anchored in a bone and is attached to an impression element 450 in accordance with FIG. 19, an impression or imprint can be made with an impression tray 453, shown in FIG. 21, which contains impression material 455. After removing the tray and the impression element 450 embedded in the impression material 455, it is clipped onto a manipulation support 563 visible in FIG. 21 whose shoulder and head are designed the same as on support 403.

Figure 22:
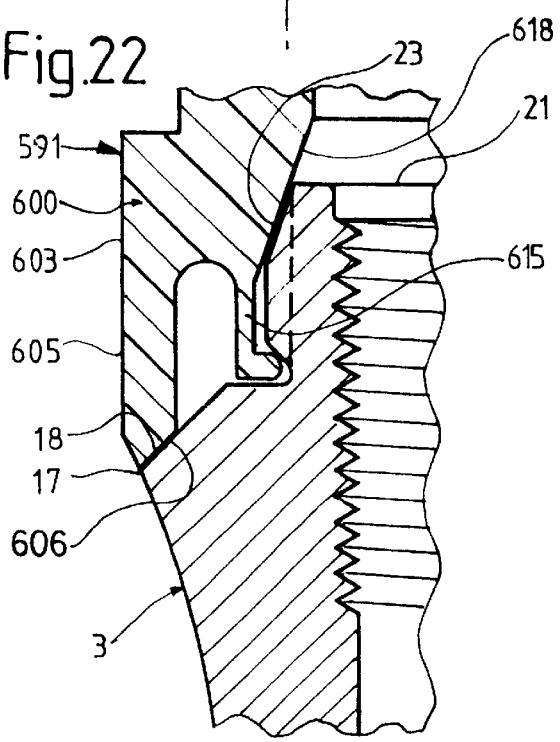

The device 591, seen in FIG. 22, has a support 3, designed the same as the support according to FIGS. 1 through 4, and an impression element 600 with a rigid wall 603. On its lower end, this has a supporting section 605 with an annular, conical supporting surface 606. The impression element 600 has fixing means and/or latching means 615, comprising a one-piece body together with the supporting section 605, and, above these, a conical interior surface section 618 which is inclined inwards as it goes up. When the impression element 600 is clipped onto the support 3, the interior surface section 618 forms the same angle with the axis of the support 3 as the circumferential surface of the conical section 23 of the support does. The impression element 600 then lies without a gap on the shoulder surface 18 with its supporting surface 606. Furthermore, the conical interior surface section 618 of the impression element 600 is supported as well as centered with very little play from the support's conical section 23 up to the upper, free end of the head 21, whereby the attachment of the impression element to the support is additionally stabilized. In spite of this additional support at the upper end of the head, the impression element can also easily be removed from the support 3 if two impression elements are being removed simultaneously from supports which are arranged at angles to each other. The impression element 600 is intended for free-positioning, for example, but could also have positioning projections for multi-positioning or uni-positioning. The device 701 seen in FIG. 23 has a support 703 which has a one-piece implant 707 and an originally separate secondary piece 708. The implant 707 forms the outer-threaded anchoring part 715 and support's 703 shoulder 717, which has an annular, conical shoulder surface 718. The implant has a pocket hole 719, which opens onto its upper end and has a section with interior threading 720. On its lower end, for example, the implant 707 has a solid cross section without any hollow space. The secondary part 708 has an inner and/or attachment section 722, which is located in the pocket hole 719 and screwed into its interior threading 720, and has a section protruding out of the implant which forms the head 721 of the support. The head 721 is, for instance, generally conical, tapers upwards, and has positioning projections and recesses distributed along its conical circumferential surface. Between the inner and/or attachment section 722 and the head 721, the secondary part 708 is provided with an annular groove 724, located slightly above the shoulder surface 718, whose upper flank forms an undercut 731 and serves as a fixing and/or attachment section. The secondary part further has an axial pocket hole 733 with an interior threading 734. The device 701 has an impression element 750 with fixing or latching means 765 and a conical interior surface section lying on the circumferential surface of the head 721. The impression element 750 is, for instance, designed for free-positioning.

Figure 23:
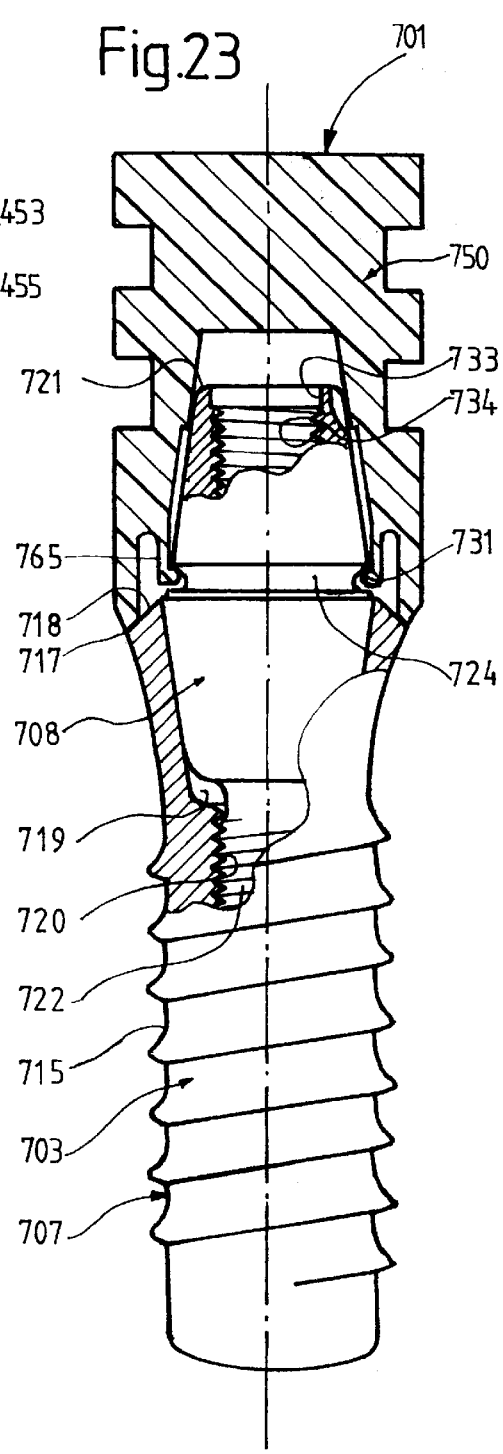

The device 801 depicted in FIG. 24 has a support 803 with an implant which, for instance, is designed the same as the implant depicted in FIG. 23 and is, like it, labeled 707 and which defines an axis 805, to which the anchoring part 715 and shoulder 717 as well, formed by the implant, are generally rotationally symmetric. The secondary part 808 of the support 803 is tilted and has an inner and/or attachment section 822, resting in the pocket hole 719 of the implant 707 and generally rotationally symmetrical to the axis 805, as well as a head 821, located outside the implant. The head 821 is coaxial and generally rotationally symmetrical to an axis 823, which forms an angle with the axis 805, and is provided with an annular groove 824, which is located slightly above the shoulder surface 718 of the implant and is rotationally symmetrical to axis 823 and whose upper flank forms an undercut. The head tapers conically upwards and has a positioning recess 827 cut near its upper end which can also be seen in FIG. 25 and which preferably is located within the angle formed by the axes 805 and 823. The secondary part 808 is provided with a hole 828 running all the way through it, which is coaxial to axis 805, and is subdivided at its lower end section into resilient tongues 830 by axial incisions 829. A screw 835 has a head which, when the tongues of the secondary part are undergoing a temporary spreading from the bottom up, can be put in its hole 828 and then lies on a narrowing of the hole formed by the tongues. The device 801 has an impression element 850. This has a wall 853, which is generally coaxial and rotationally symmetric to axis 823, but has, however, at its lower end a supporting surface 856 which is coaxial and rotationally symmetric to the axis 805. The fixing and/or latching means 865 of the impression element 850 are generally rotationally symmetrical to the axis 823 and, when the device is assembled, engage with the undercut formed by the upper flank of the annular groove 824, such that they press the impression element 850 against the shoulder surface 718 of the implant. Above the fixing or latching means 865, the impression element 850 has a conical interior surface section which is held with little play by the conical surface of the head 821. The impression element 850 further has a positioning projection 871, also seen in FIG. 25, which protrudes into the positioning recess 827. The head 821 of the secondary part 808 can, if necessary, be ground for the formation of a construction before or after an impression element 850 has been clipped on, such that its conical circumferential surface and/or its flat front face is partially replaced by a ground surface 881, indicated by dotted lines. Then the impression element 850 can also still be stably attached to the support 803 if the head 821 is ground for the attachment of the impression element. Additionally, the head of the manipulation support can be ground to match.

The device 901 shown in FIG. 26 has a support 903. This is designed similar to the support 803 according to FIG. 24 and has an implant 707, an inclined secondary part 908 with a hole 928 running through it, and a screw 935. The secondary part 908 differs from the secondary part 808 seen in FIG. 24 in that it does not have any incisions which correspond to the incisions 829 and is designed such that the screw 935 can be inserted into the hole 928 from above. The device 901 further has an impression element 850 which is designed the same as the impression element seen in FIG. 24.

The device 1001 depicted in FIG. 27 has a support 1003 with an implant 1007, essentially rotationally symmetric to an axis 1005, and a secondary part 1008. The implant 1007 has a shoulder 1017 with an annular, flat shoulder surface 1018, perpendicular to axis 1005, and a stepped pocket hole 1019 which opens onto its upper end. The secondary part 1008 has an inner and/or attachment section 1022, resting in the pocket hole 1019, and a head 1021. This is generally rotationally symmetric to an axis 1023, which forms an angle with the axis 1015, but, at its connection to the section 1022, has an annular, flat supporting surface, perpendicular to axis 1005; which lies on the inner region of the shoulder surface 1018. The secondary part 1008 further has a hole 1028 running through it whose lower section is coaxial to the axis 1005 and whose upper section is coaxial to the axis 1023 and is provided with an interior threading 1029. On its lower end, the secondary part 1008 is subdivided into spreadable tongues by incisions and detachably connected with a screw 1035 to the implant 1007, whose head can be introduced into the secondary part from below, just as that of the device seen in FIG. 24. The impression element 1050 of the device 1001 has an annular, flat supporting surface 1056 which, when the device is assembled, is perpendicular to the axis 1005 and lies on the outermost region of the shoulder surface 1018. The impression element 1050 further has on its lower end a collar-shaped extension 1057, which points down coaxally to the axis 1005 at the outer edge of the supporting surface 1056, covers the outer edge of the shoulder surface 1018 with very little axial play at most, and centers the lower end of the impression element coaxially to the axis 1005. When the impression element 1050 is used, the extension 1057, moreover, presses downwards on the patient's soft tissue surrounding the shoulder 1017 so that one can do without the so-called placing of sutures, often necessary, that is, the fixing of the soft tissue with the aid a suture. The device 1001 shown in FIG. 27 can likewise serve to form a bridge together with at least one additional, identically formed device.

The support 1103 seen in FIG. 28 comprises a one-piece implant and has a shoulder 1117 with a conical shoulder surface 1118 as well as a head 1121 with a cylindrical section 1122 and a conical section 1123. An annular groove 1124 is provided between the shoulder 1117 and the head 1121. The annular front surface at the free end of the head is provided with positioning projections 1125 and positioning recesses 1127, 1128, following each other alternately along the circumference, where several first recesses 1127 are designed the same and a second, broader recess 1128 is provided.

The cap-shaped impression element 1150 depicted in FIG. 29 has a wall 1153 which at its lower end has a supporting section 1155 with a conical supporting surface 1156. The impression element further has fixing and/or latching means 1165, as well as positioning projections 1171. The impression element 1150 fits with the support 1103 shown in FIG. 28 and can be clipped on it. The positioning projections 1171 then engage with the positioning recesses 1127, 1128. The positioning projections 1171 are all designed the same and enable multi-positioning but can, however, be designed for a uni-positioning or left off. When the impression element 1150 is attached to the support 1103, the supporting section 1155, the supporting surface 1156, and the fixing and/or latching means 1165 are coaxial to the axis of the support, while the upper main part of the impression element is at an angle to the support.

Figure 30:
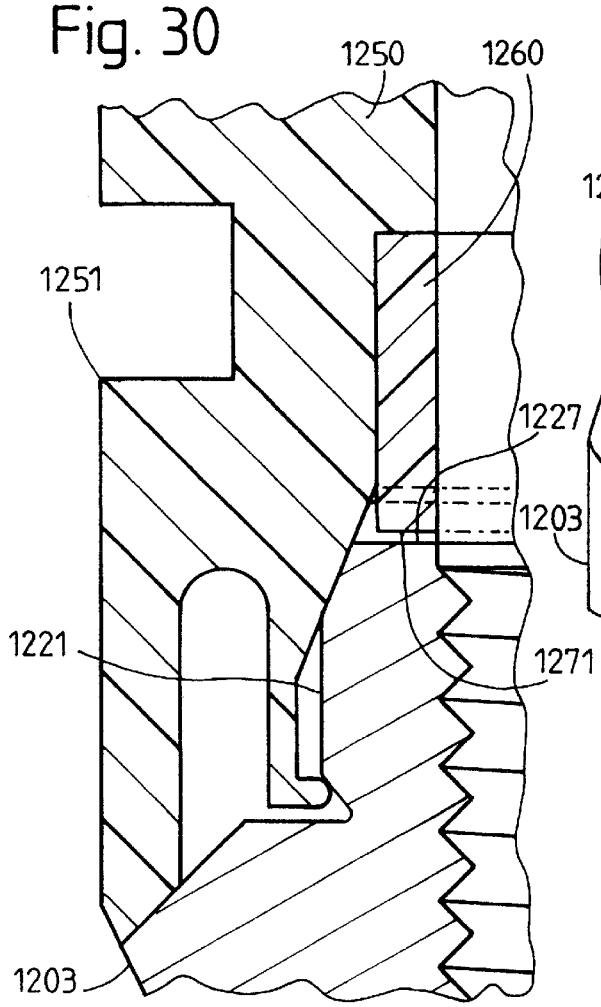
Figure 31:
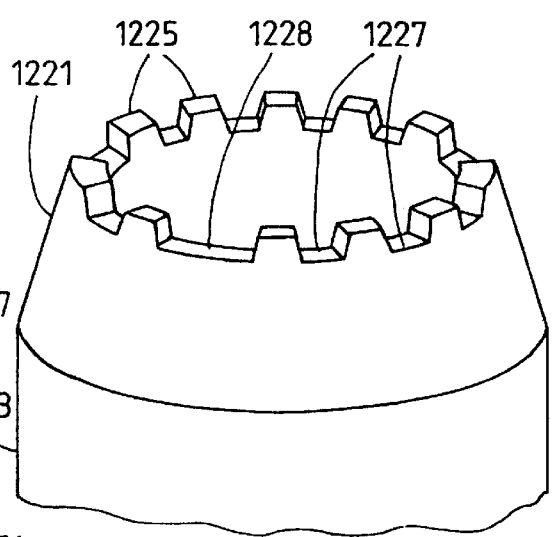
Figure 32:
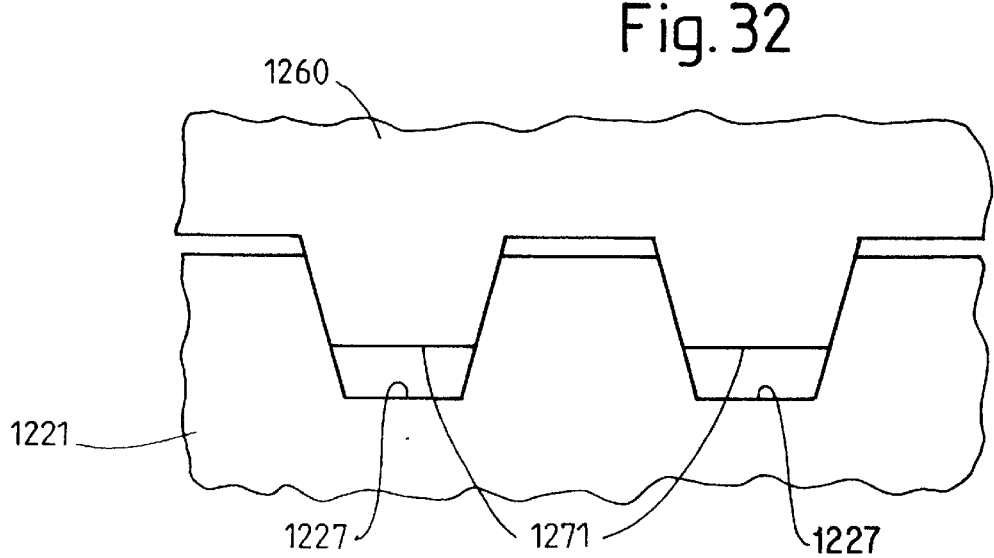

The device shown in FIGS. 30, 31, 32 has a head 1221. The latter has positioning projections 1225, first positioning recesses 1227 and a second positioning recess 1228. The support 1203 is similarly designed to the support 1103, however differs from this in that the projections 1225 and the recesses 1227, 1228 are trapezoidal in a radial viewing direction. Both lateral surfaces of each recess 1227, 1228 are inclined away from each other from their base up, such that the recess broadens from the base up.

The impression element 1250 has a one-piece cap 1251 and an essentially hollow, cylindrical, case-shaped positioning insert 1260, which was originally separate and is located in its interior space and attached in a hollow cylindrical section of the cap, namely pressed in and/or glued in. This is provided on its lower end with positioning projections 1271 which, for instance, are all designed the same and for multi-positioning. The projections 1271 are trapezoidal in a radial viewing direction and designed such that their lateral surfaces protrude between the lateral surfaces of the first recesses 1227 of the support head 1221 with very little play, at most, when the device is assembled.

Figure 33:
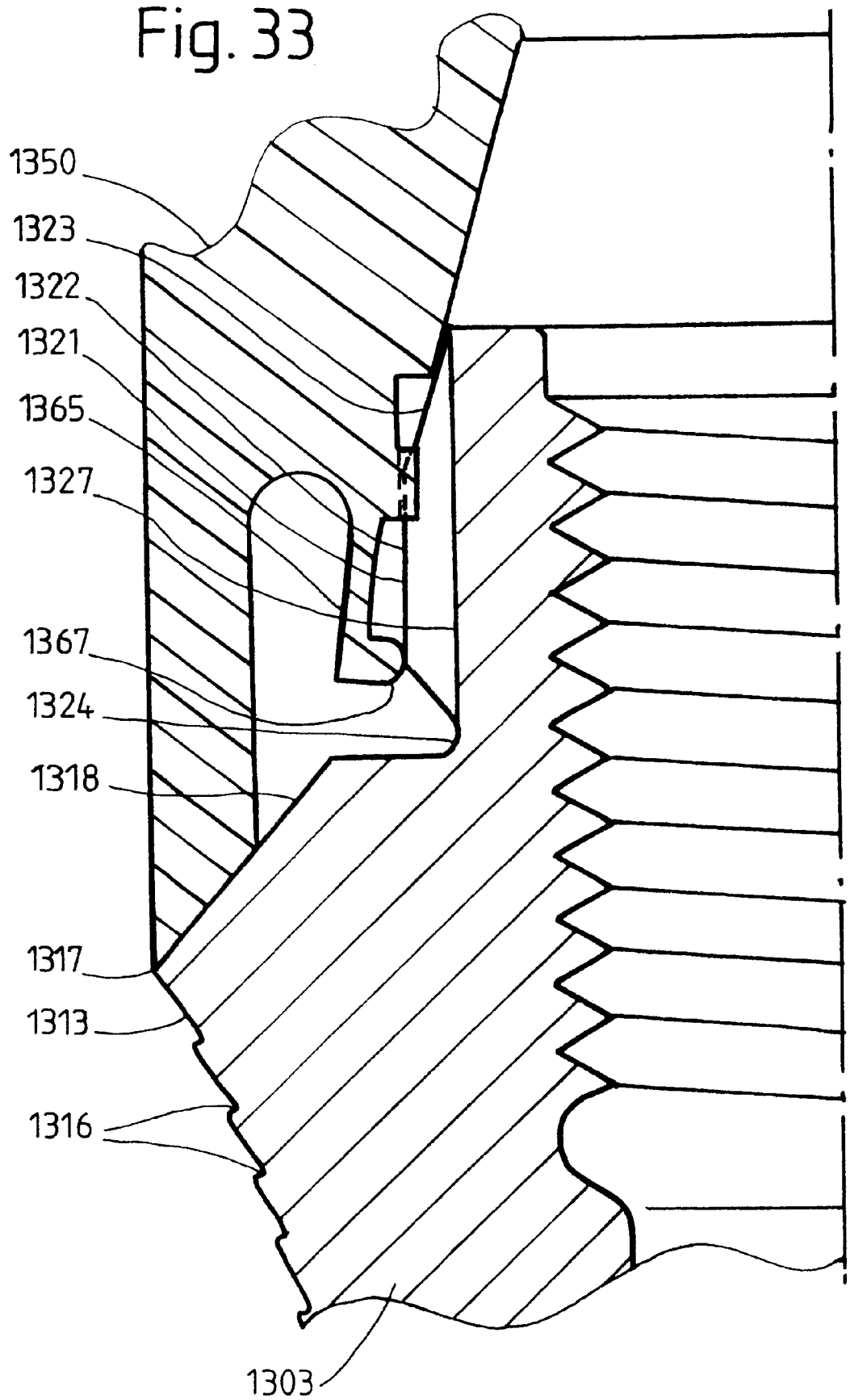
Figure 34:
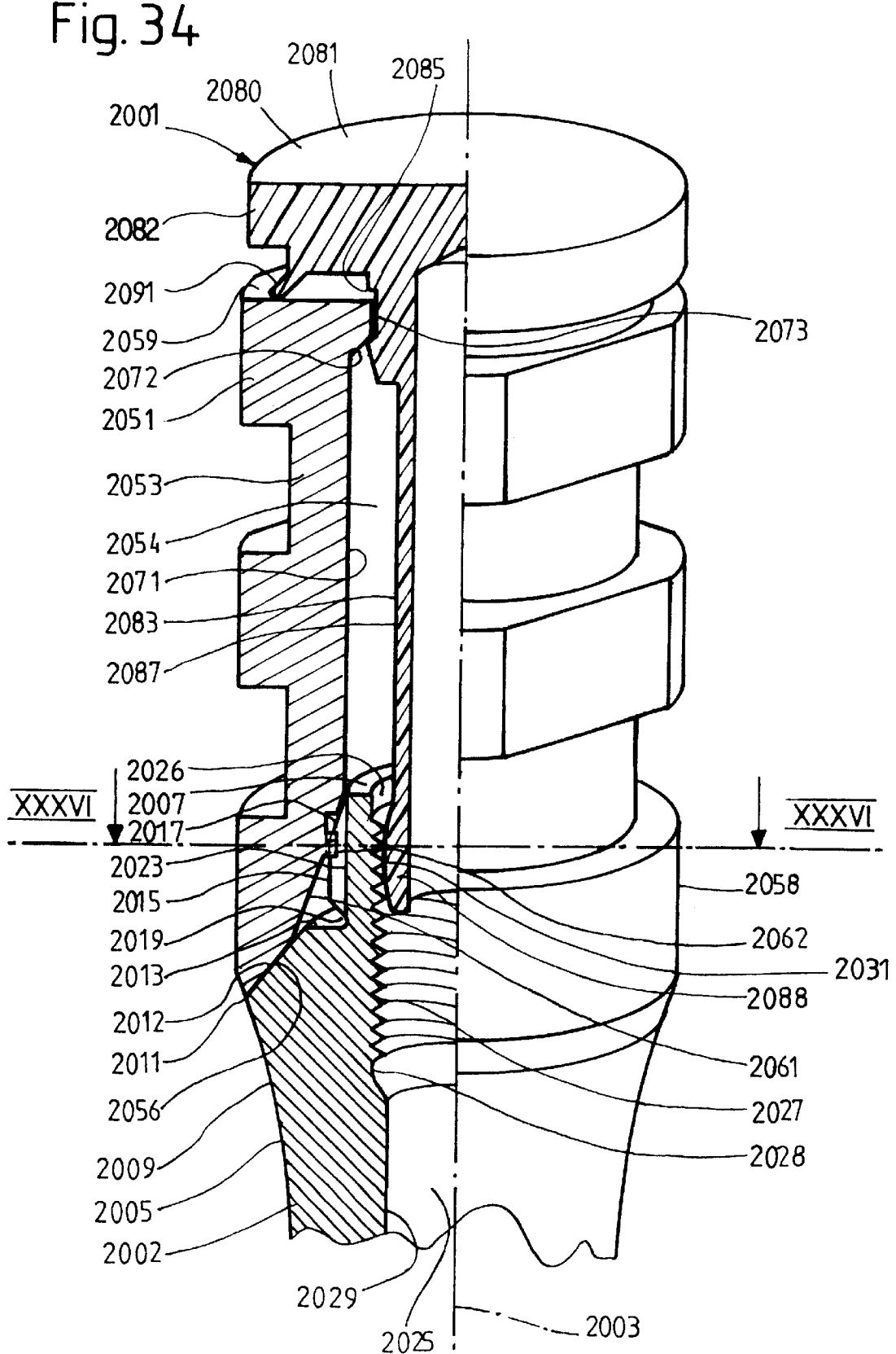
Figure 35:
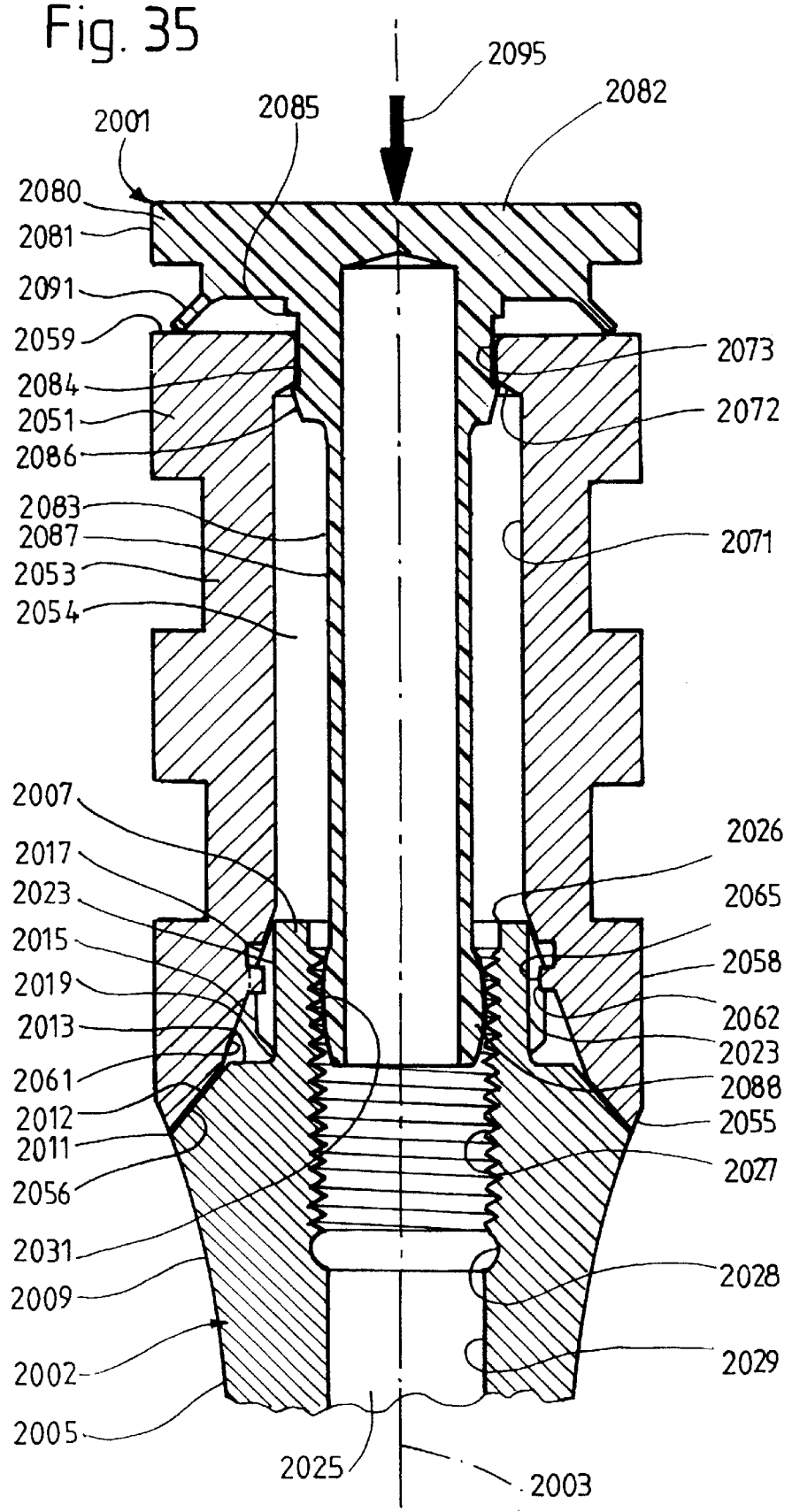

The device seen in FIG. 33 has a support 1303. Its trumpet-shaped section 1313, broadening towards the shoulder 1317, is provided with several depressions 1316, spaced apart from each other in an axial direction, namely annular grooves. The support 1303, apart from these depressions or grooves, is designed essentially like the support 3 and has, like it, a conical shoulder surface 1318 and a head 1321 with a generally cylindrical section 1322, a conical section 1323, as well as a groove 1324, situated between the shoulder surface 1318 and the cylindrical section 1322. Both the sections 1322, 1323 are provided with positioning recesses, of which one of the first positioning recesses 1327 is visible. The impression element 1350 seen in FIG. 33 is designed similarly to the impression element 50, but has an additional conical interior surface, lying on top of the upper end of the conical head section 1323, and positioning projections designed for multi or uni-positioning. The fixing means 1365 are in part designed similarly to the fixing and/or latching means 65, 115 and have a thin, case-shaped, deformable section and, on the bottom end of this, a nose 1367 which points approximately radially inwards. When the impression element lies on the shoulder surface 1318, however, the nose 1367 does not engage with the annular groove 1324. In this version, the nose 1367 is actually only squeezed against the lower end of the cylindrical section 1322 on its cylindrical circumferential section. The elastic deformation of the case-shaped section of the fixing means 1365, cylindrical in its unstressed state, thus creates the necessary tension or binding power. Additionally, the fixing means 1365 can be subdivided by incisions into tongues in the same way as the fixing means 215 in FIG. 8.

The device 2001 seen in FIGS. 34 through 37 has a support 2002. This is essentially designed identically to the support 3 and exclusively comprises a one-piece implant, likewise labeled 2002. This is made of a metallic material, for example titanium. The implant 2002 has an axis 2003 and is essentially rotationally symmetric to it. The implant 2002 has an anchoring part 2005 below and a head 2007 above. The free end of the head forms the upper end of the whole implant 2002. The anchoring part 2005 has a generally cylindrical section below, not visible, with an outer threading and a trumpet-shaped section 2009 which spreads out upwards from the generally cylindrical section. At the upper, wider end of the trumpet-shaped section 2009, a shoulder 2011 is provided which has a conical shoulder surface 2012, inclined inwards going up towards the head. This forms an angle of 40° to 50°, and for example 45°, with the axis 2003. A flat annular surface 2013, perpendicular to the axis 2003, adjoins the upper, narrower end of the conical shoulder surface 2012.

The head 2007 projects upwards from the annular surface 2013 and has a generally cylindrical head section 2015, essentially parallel to the axis 2003, and a generally conical head section 2017 which tapers upwards from this to the free end of the head. The head section 2015 which is parallel to the axis is separated from the upper end of the shoulder 2011 by an annular groove 2019, curved to be concave in an axial cross section. On its free end, the head has a flat, annular front face. Both head sections 2015, 2017 are generally rotationally symmetric to the axis 2003 and/or at least each have a cover surface, namely cylindrical or conical, which is rotationally symmetric to the axis. Both the head sections 2015, 2017 together, however, form a positioning section and are provided with positioning recesses or grooves 2023 which are distributed along the axis 2003 and are parallel to it. In this exemplary embodiment, however, these form positioning surfaces which are curved to be concave in a cross section perpendicular to the axis 2003. The positioning grooves 2023—or at least the deepest part of these in the cross section—stretch over the whole length of the head section 2015, which is parallel to the axis 2003, and to the thinner end of the conical head section 2017 at least nearly, for instance exactly as well, and moreover also to the free end of the of the head and thus to the upper end of the whole implant. The section of each positioning groove 2023 which is located in the region of the head section 2015 parallel to the axis forms in the cross section an arc which is at most a semicircle and is namely smaller than a semicircle. The sections of the positioning grooves 2023 located in the region of the generally conical head section 2017 then form smaller arcs and, at the thinner end of the conical head section, run into the free end of the head. Between the positioning grooves 2023, the two head sections 2015, 2017 have surface sections, which form parts of a cylindrical or conical surface. The positioning grooves 2023 preferably show several identical first positioning grooves, as well as a second, broader and deeper positioning groove, but could possibly all be designed and sized the same.

The conical casing surface of the generally conical head section 2017 forms an angle with the axis 2003 which is smaller than the angle formed with the axis 2003 by the conical shoulder surface 2012 and which is coordinated with the distance of the conical head section from the shoulder such that the extension of the conical surface defined by the conical head section intersects with the shoulder 2011 within the outer edge of the conical shoulder surface 2012 and namely intersects with the inner half of the conical shoulder surface 2012, for instance, or possibly the flat annular surface 2013. Measured from the flat annular surface 2013 to the free end of the head, the axial measurement or height of the head 2007 is 2 mm at the most, preferably 1.2 mm to 1.8 mm, and for example about 1.5 mm. The combined axial measurement of the head section 2025 which is parallel to the axis and the annular groove 2019 are, for example, about 1 mm. The axial measurement of the generally conical head section 2017 is, for instance, about 0.5 mm. generally conical head section 2017 is, for instance, about 0.5 mm.

The implant 2002 has a pocket hole 2025 which is coaxial to the axis 2003. This has a mouth 2026, located at the free end of the head and formed by a very short cylindrical hole section, and, moving down from this in order, a metric, for example, interior threading 2027, a groove 2028, a smooth—that is, without threading—cylindrical hole section 2029, and a base, not visible.

The device 2001 further has an impression element or an impression cap 2051. This is case-shaped and has a rigid wall 2053 which delineates an interior space 2054, open below and above. The lowest region of the wall 2053, annular in cross section, forms a supporting section 2055 and has an annular, conical supporting surface 2056 at its free end. Its outer edge forms the lowest point of the impression cap and bounds the opening at which the interior space 2054 opens into the surroundings of the impression cap 2051. When the latter is connected to the support or implant 2002, the supporting surface 2055 forms the same angle with the axis 2003 as the shoulder surface 2012 and lies without a gap on at least a part of this, where both surfaces 2012, 2056 in particular lie on each other out to their outer edges. At the outer edge of the supporting surface 2056, the casing and/or outer surface 2058 of the impression element has a section which touches the casing and/or outer surface 2014 of the support and, moving up from this, is inclined outwards the same or similarly to the neighboring section of the casing and/or outer surface of the trumpet-shaped section 2009 of the implant such that both of the casing and/or outer surfaces adjoin each other seamlessly, continuously, and at least nearly smoothly and steadily at the shoulder 2011. The generally cylindrical main section of the surface 2058 then adjoins the inclined section, which is only short, of the casing and/or outer surface 2058. This main section is, however, provided with annular grooves and axial flattened surfaces or grooves, which provide the structure for the exterior form of the impression cap. On its upper end, which is on the opposite side from the implant, the cap has an annular, flat end surface which forms an angle with the axis 2003, namely is perpendicular to the axis, and is labeled in the following as fixing surface 2059.

Inside, the impression element or the impression cap 2051 has an interior surface 2061 which adjoins the upper, thinner end of the conical supporting surface 2056 and is generally likewise conical, but steeper. This forms the same angle with the axis 2003 as the conical surface of the generally conical head section 2017. The generally conical interior surface 2061 is, however, subdivided into two height regions by a positioning section 2062, particularly clearly visible in FIGS. 34 and 35. The positioning section 2062 is located approximately at the height at which the head section 2015 which is parallel to the axis is connected to the generally conical head section 2017. Above the positioning section 2062, for example, a narrow annular groove 2063 is also provided. However, in any case, above the positioning section 2062 and the annular groove 2063, the generally conical inner surface 2061 has a section, located at the height or axial region of the conical head section 2017, which is supported with very little play by the conical surface of the generally conical head section up to the free end of the head.

The positioning section 2062 has positioning projections 2065, distributed along the axis 2003. Each positioning projection 2065 protrudes into a positioning groove 2023. The axial measurement of each positioning projection 2065 is essentially smaller than the total axial measurement of both the head sections 2015, 2017 and is preferably 30% at most of the total axial measurement of both of the head sections 2015, 2017 and of the positioning grooves as well as of the whole head 2007, naturally. The positioning projections are thus at a distance from the lower end of the head section 2015, parallel to the axis, and from the upper end of the conical head section 2017 and are located at the height indicated for the positioning section 2062. The positioning projections have angular surfaces which, in a cross section perpendicular to the axis 2003, form coaxial arcs to the axis 2003. The upper section of each angular surface 2066, located further from the shoulder 2011, is parallel to the axis 2003 and comprises a section of a cylindrical surface. In its lower region, nearer to the shoulder 2011, each angular surface has, according to FIG. 37 an incline 2067, inclined towards the outside as it goes down, which is formed by a section of a conical surface. A free space is provided between each angular surface 2066 and the floor of the positioning groove 2023 which contains the projection concerned, which space's radial measurement at the deepest point of the groove is equal, for example, to at least half of the depth of the groove. In a cross section perpendicular to the axis 2003 according to FIG. 36, the side surfaces 2068 of the positioning projections 2065 are bowed and are separated from the surfaces of the grooves 2023 at most by very narrow gaps. The projections 2065 thus have very little play in the grooves along a circle concentric to the axis 2003 and tangentially to this circle. Spaces 2069 are provided between the positioning projections 2065 of the cap, into which the projections between the positioning grooves 2023 of the head or the sections of both the head sections 2015, 2017 protrude with rather little radial play.

If all the grooves 2023 are designed the same, all the projections 2065 are also designed the same. As already described, however, several identical first positioning grooves and a broader and deeper second positioning groove can be provided. Then, the cap can be designed for multi-positioning and only have identical projections. In this case, the sides of the positioning projection which protrudes into the second positioning groove are separated from the groove surface by broad spaces. On the other hand, if the cap is designed for uni-positioning and has several first projections which fit in the first grooves and a second positioning projection which only fits in the second positioning groove, it can likewise engage with the second positioning groove with very little lateral play.

Above the conical interior surface 2061, the cap's interior space 2054 has, in order from bottom to top, another cylindrical interior space section 2071, a conical annular surface 2072, tapering upwards, which forms an angle with the axis 2003, and a narrower cylindrical interior space section, which serves as a guiding hole 2073 and whose upper end forms the upper mouth opening of the interior space 2054. The cap 2051 is made, for example, of a metallic material, however, could instead be made of synthetic material.

The device 2001 has fixing means 2080 with a one-piece connection element 2081, generally rotationally symmetric to the axis 2003, for detachably connecting the impression element or the impression cap 2051 atop the implant. The connection element 2081 is made of thermoplastic synthetic material and has a circular head 2082, for example, as well as a shaft which is connected to this and comprises a case 2083. Near its end which is connected to the head 2082, the case 2083 has a cylindrical, relatively thick-walled, stiff guiding section 2084, which penetrates the guiding hole 2073 of the cap 2051 and is guided, displaceable axially, into the guiding hole 2073 with little radial play. At the upper end of the guiding section 2084, located outside the cap, a thickening which serves as a stop 2085 is provided on the exterior. At the end of the guiding section 2084 located in the interior space 2054, an annular thickening is provided on the exterior which is barb-shaped in an axial cross section and which forms a snap section 2086. This is designed such that it can be pressed, by elastic deformation of the case 2083, from outside the cap through the guiding hole 2073 and then snap into the annular surface 2072 and catch behind this such that the connection element 2081 is held by the cap so as to be moveable but not so as to come off. When being held by the cap 51, the connection element can be moved back and forth in an axial direction in a region bounded by the stop 2085 and the snap section 2086. The middle section 2087 of the case 2083 adjoins the snap section 2086. The middle section 2087 essentially has thinner walls than the guiding section 2084 and has a length several times its outer diameter. The middle section 2087 is thus easily elastically bendable. The end section of the case 2083 which is at the opposite side from the head 2082 serves as a fixing section 2088, forms a complete ring in a cross section, and has a curved outer surface which in an axial cross section is slightly convex and whose maximal outer diameter is somewhat greater than the outer diameter of the middle section 2087. The free end of the case 2083, which is opposite the head 2082 and formed by the fixing section 2088, is open.

When the impression element or the impression cap 2051 is connected to the support or implant 2002, the case 2083 protrudes into the pocket hole 2025 of the implant such that at least one part of the fixing section 2088 is located inside the interior threading 2027. Subjected to elastic deformation, the fixing section 2088 is deformable in an approximately radial direction, that is, can be compressed. When relaxed and not deformed, the fixing section 2088 has a maximum outer diameter which is a little bit greater than the interior diameter of the interior threading 2027. The interior threading 2027 of the support thus forms a fixing section and/or attachment section 2031 on which, or in which, the fixing section 2088 of the connection element is detachably jammed fast. On its side which faces the cap, the head 2081 is provided with elastically deformable pressing means 2091, which engage with the fixing surface 2059 of the cap and—as will be described in closer detail—exert pressure on the cap, at least when the device 2001 is assembled. The pressing means 2091 comprise an elastically deformable annular lip, which is connected to the head 2081 and which, moving away from the head, is inclined outwards. However, these could be subdivided by incisions and replaced by a wreath of separate lips distributed along the axis.

Now, the use of a support or implant 2002 and the impression cap 2051 will be described. A dentist makes a hole in the bone of the lower or upper jaw of a patient and places the implant 2002 forming the support into the hole such that the anchoring part 2005 of the implant is anchored in the bone, while the shoulder 2011 and the head 2007 protrude from the bone like in FIG. 9. When, after a certain time period, the implant has taken in the bone, the dentist sticks the impression cap 2051, provided with the connection element 2081, over the head 2007 of the implant, against its shoulder 2011, and simultaneously positions the cap in the desired rotation position. While putting on the cap, the dentist pushes the fixing section 2088 of the connection element 2081 into the pocket hole 2025 of the implant at the same time. In the process, the fixing section 2088 lands in the interior threading 2027 and, subjected to elastic deformation while being pushed in, is compressed in an approximately radial direction. When the cap lies with its conical supporting surface 2056 on the conical shoulder surface 2012 of the implant, the dentist can press on the head 2082 of the connection element 2081 with his finger or some instrument, exercise on this a force indicated in FIG. 35 by an arrow, and press the head 2082 towards the cap until the stop 2085 is against the cap. In this process, the fixing section 2088 gets pushed a little deeper still into the pocket hole 2025 and is then jammed fast in the interior threading 2027 or in the fixing section formed by this. The lip forming the elastic pressing means 2091 then exerts an axial force on the cap. This force presses the cap against the shoulder surface 2022 of the implant such that the cap lies on the shoulder surface without a gap.

The dentist can now press an impression tray, filled with possibly warmed, soft, plastically deformable impression material, over the impression cap against the gingiva covering the bone, like in FIG. 10. This, as well as the parts of the device 2001 projecting from it and, possibly, natural teeth still present in the vicinity of the device produce an impression in the impression material and are imprinted in it such that the impression material forms an imprint surface. After the thickening and hardening of the impression material, the dentist lifts the impression tray and the impression cap, which is embedded in the impression material, approximately parallel to the axis 2003 of the implant off of this. In this process, the fixing section 2088 is pulled out of the interior threading 2027 and the whole pocket hole 2025 by overcoming the jamming, fixing, and frictional force holding it in. The tray, the impression material contained in this, and the impression cap 2051 embedded in this with the connection element 2081 held by this are now taken out of the patient's mouth and, for example, brought to a dental laboratory.

There, the impression element or impression cap detachably connected to a manipulation support or manipulation implant. This has an anchoring part, a head, a shoulder, and an axial pocket hole with inner threading which opens onto the head. The upper part of the anchoring part which borders the shoulder, the shoulder, the head, and the pocket hole of the manipulation implant are designed the same as in the implant 2002 When being connected to the manipulation implant, the impression cap 2051 is positioned the same and detachably connected to the manipulation implant by means of the connection element 2081 as it was connected to the implant 2002. The manipulation implant together with the impression cap now forms a device. The impression cap then lies with the conical supporting surface 2056 on the annular, conical shoulder surface of the manipulation support or manipulation implant. After that, the same way as in FIG. 13, a master model made of modeling material is formed, in which are anchored the section of the manipulation support or implant protruding from the impression material and particularly its anchoring part. When a dental technician or some other person removes the tray, along with the impression material and the impression cap 2051 from the master model, the fixing section 2088 of the impression cap is pulled out of the manipulation implant. Then, a cap is detachably connected to the manipulation support or the manipulation implant and a structural element is built on. If the structural element has the desired form, it is removed from the manipulation support, introduced into the patient's mouth, and, for example, connected to the implant using a section which is screwed into the inner threading 2027 of the support or implant 2002.

If a dentist inserts into the jaw of a patient two implants designed to hold a bridge or a prosthesis of several teeth, the dentist can detachably connect an impression cap on each of these implants. The dentist can press one same impression tray filled with impression material over the impression caps such that the latter become embedded in the impression material. After the impression material has hardened, the dentist can remove the tray and the two impression caps, now held in the impression material, from the two implants in the same way as in FIG. 15. This is also possible, then, when the axes of the two implants are at an angle to each other. While the impression caps are being removed from the implants, the cases 2083 of the connection elements then temporarily become somewhat elastically bent, for example.

Using the two impression caps, a dental technician can then produce a master model with two manipulation implants and build on these a structural element comprising a bridge or prosthesis.

Figure 38:
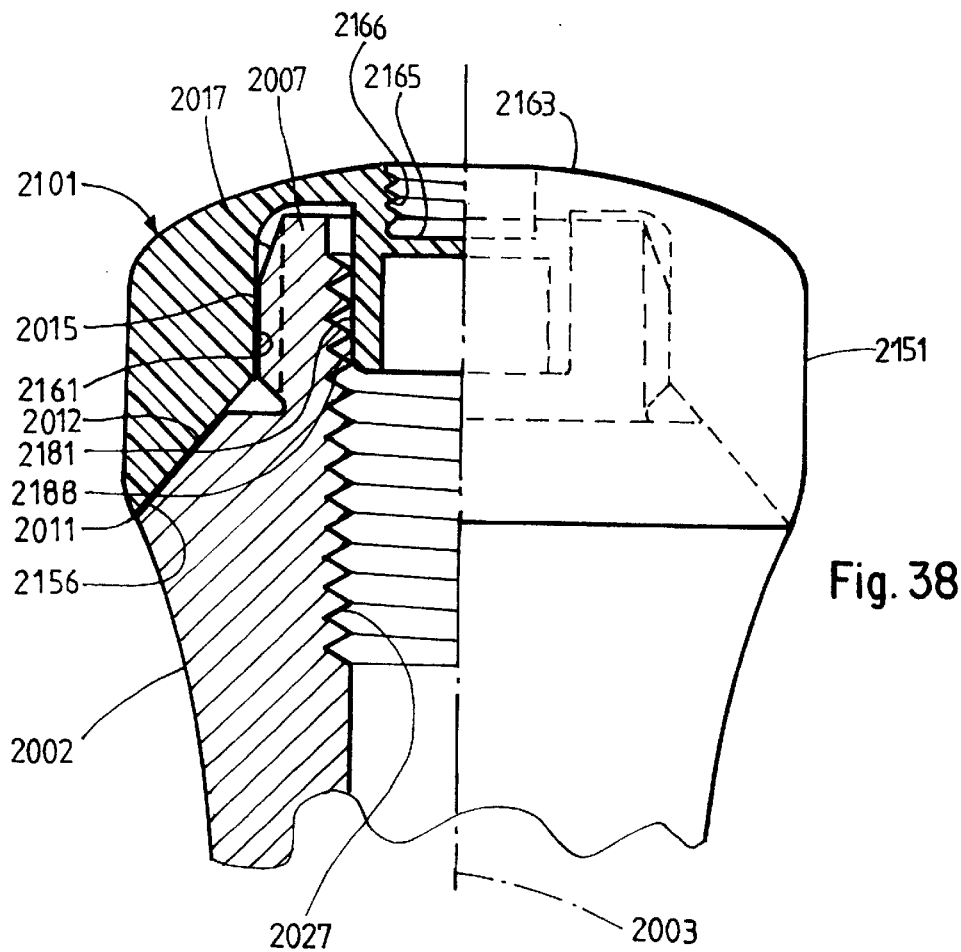

The device 2101 seen in FIG. 38 has a support or an implant. This support, or this implant, is designed the same as it is in the device shown in FIGS. 34 to 37 and is labeled with 2002 as in these figures. The device 101 further has a healing element or a healing cap 2151. This has a conical supporting surface 2156, which lies without a gap on the conical shoulder surface 2012 of the implant, and a cylindrical interior surface 2161, which is guided and supported with very little radial play by the generally cylindrical head section 2015, which is parallel to the axis. The healing cap doesn't have a positioning projection and is thus designed for free-positioning. The healing cap 2151 has a cover section 2163, which laps a small distance over and covers the free end of the head 2007. In its center, this has a short axial pocket hole 2165 with an interior threading 2166.

The connection element 2181, which serves to connect the healing cap 2151 to the implant 2002, is made up of a hollow cylindrical case which, together with the healing cap, forms a one-piece body made of thermoplastic synthetic material. The section of the case on its open free end, which protrudes into the interior threading 2027 of the pocket hole 2025 of the implant 2002, serves as a fixing section 2188 and is jammed fast in the interior threading 2027. In order to remove the healing cap from the implant inserted in the mouth of a patient, the dentist can screw an aiding tool with an exterior threading into the interior threading 2166 of the healing cap and remove the cap, along with the connection element, from the implant. However, the dentist can instead also grab and remove the healing cap with his fingers or forceps.

Figure 39:
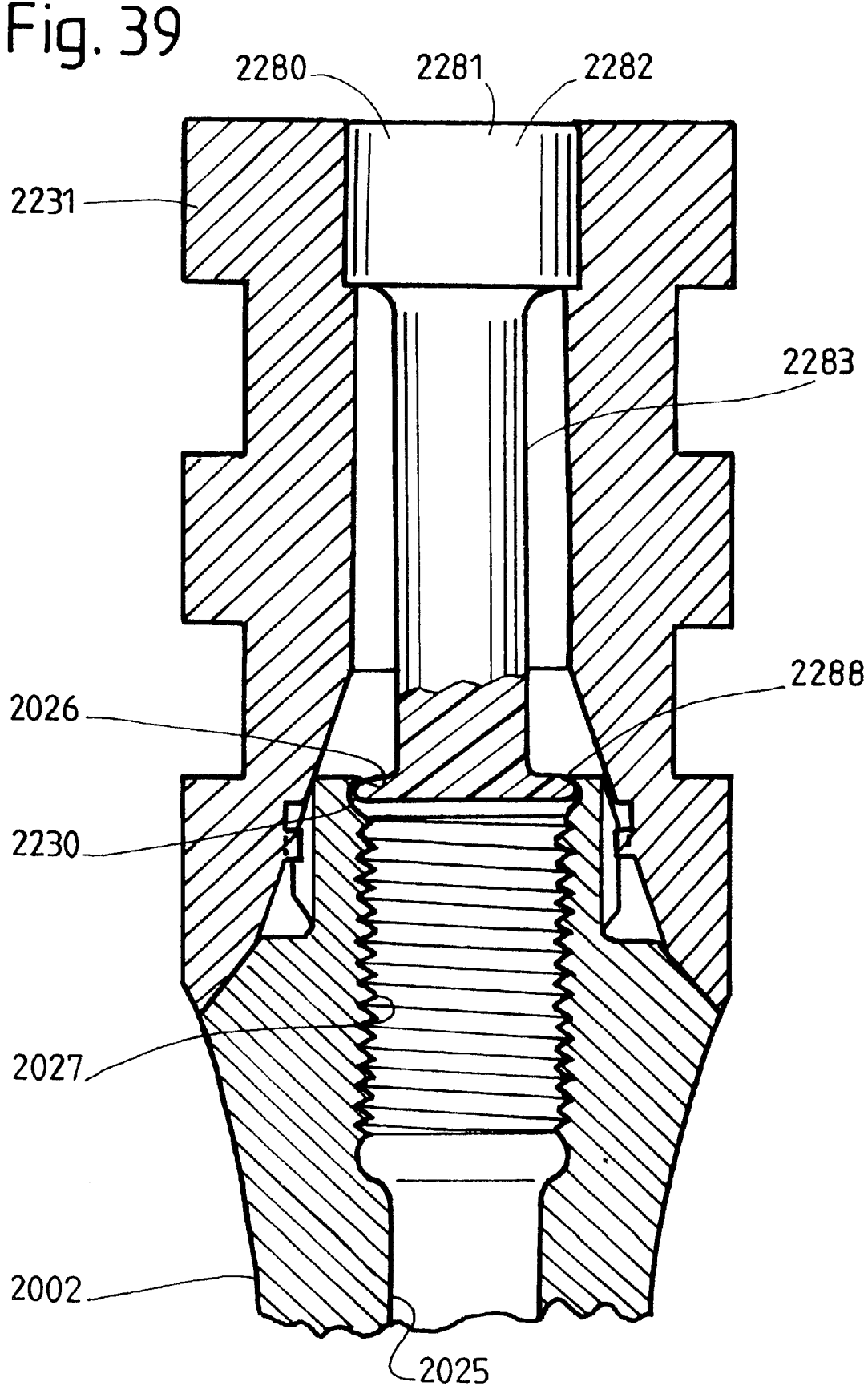
Figure 40:
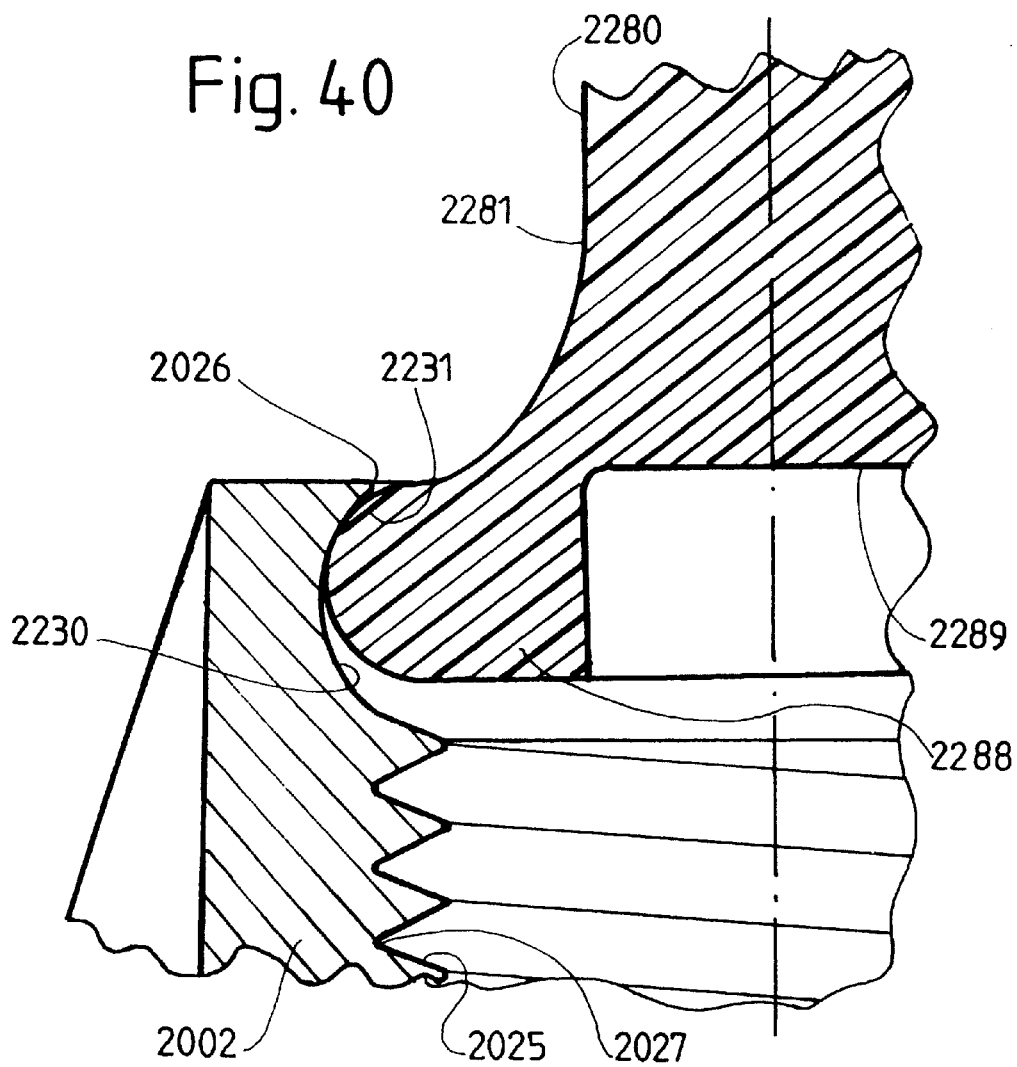

The device seen in FIG. 39 has a support which is, for example, designed similarly to the support shown in FIGS. 34 to 37 and, like it, is labeled 2002. The implant seen in FIG. 39 forming the support once again has an axial pocket hole 2025 with an mouth 2026 and an interior threading 2027. Between this and the rim of the mouth, however, an annular groove 2230, also visible in FIG. 40, is provided. The annular groove 2230 is curved to be concave in an axial cross section and forms and/or bounds a fixing section and/or connection section 2231.

The impression element 2251 shown in FIG. 39 has an axial, stepped hole running through it. Furthermore in FIG. 39, fixing means 2280 are visible which are made up of a one-piece, longish connection element 2281, originally separate and made of synthetic material. On its upper end, this has a head 2282 which sits fast and immobile in a cylindrical extension of the hole of the impression element 2251 and, for example is pressed into this and/or glued in. The connection element 2281 has an elastically bendable, longish section or shaft 2283, which points downwards away from the head. Between its circumferential surface and the interior surface of the impression element, an annular space is provided such that the shaft can be somewhat bent in the interior space of the impression element. At the bottom end of the shaft, a disc-shaped fixing section 2288 is provided with an edge that is convex in an axial cross section. The edge-region of the disc-shaped fixing section 2288 forms a nose which, with respect to the shaft, points radially outwards. The fixing section 2288 is elastically deformable and can be somewhat elastically compressed, particularly in the radial direction.

To connect the impression element 2251 to the support 2002, the impression element, together with the connection element 2281, which is connected to it so as not to move, is stuck onto the support. In the process, the fixing section of the 2288, subjected to temporary elastic deformation, namely radial compression, can be latched into the annular groove 2230. The fixing section 2288 of the connection element 2281 then lies on the support's 2002 fixing section 2231, which forms an undercut, and presses the supporting surface of the impression element 2251 against the shoulder surface of the support 2002. For removing the impression element 2251 from the support 2002, the impression element, together with the connection element fixed in it, can come off of the support and the fixing means 2230, 2288 can disengage from each other. The support 2002, or the implant, is made from a firm metallic material, it is true. At the edge of the mouth 2026, however, the fixing section 2231 of the support forms a rather narrow lip and can thus possibly also be slightly deformed elastically when the connection element 2281 is latched and unlatched.

The fixing means 2280 partially shown in FIG. 40 have a connection element 2281 which is designed similarly to the one in FIG. 39 but in addition has a recess 2289 on the front side of the disc-shaped fixing section 2288. This increases the ability of the fixing section 2288 to elastically deform, so that it can be more easily latched into the annular groove 2230 of the support 2002 and unlatched from this again.

Figure 41:
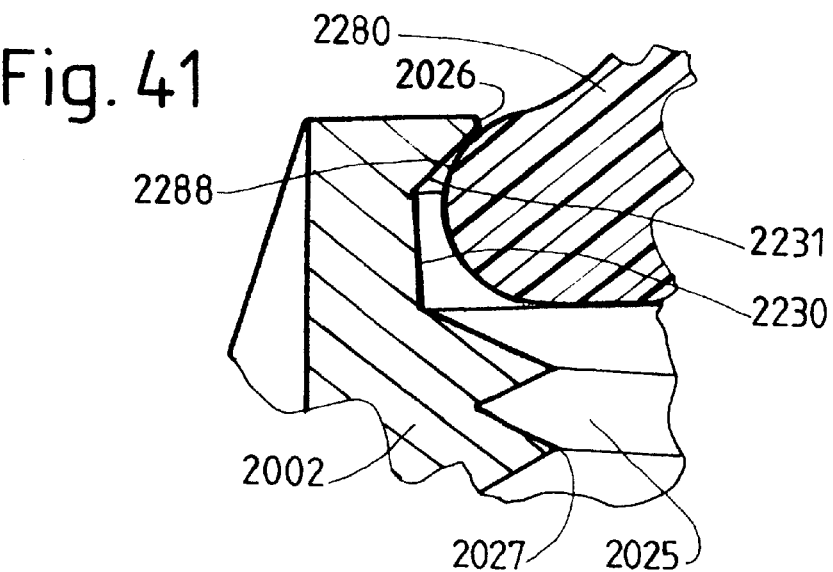

The device partially shown in FIG. 41 is similarly designed to the devices in accordance with FIGS. 39, 40. The annular groove 2230 of the support 2002 depicted in FIG. 41 is, however, not curved in an axial cross section, but trapezoidal. The fixing section 2231 of the support thus has a surface which is inclined from the floor of the annular groove 2230 towards the mouth 2026 and with which the fixing section 2288 of the fixing means 2280 engage when the device is assembled.

Figure 42:
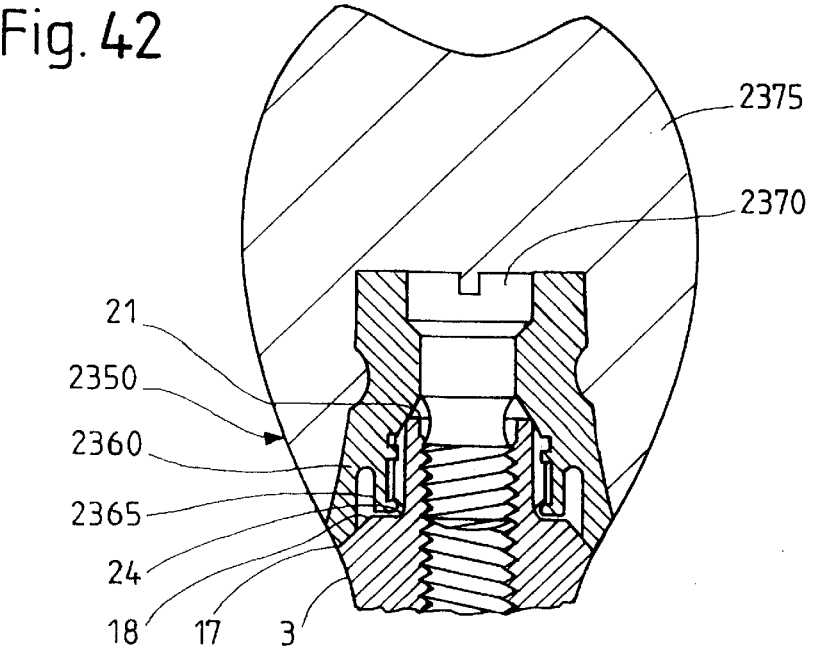

The device shown in FIG. 42 has a support which is designed similarly, for example, to the support shown in FIGS. 1 through 4 and, like it, is labeled 3. A structural element 2350 has a metallic cap 2360, which lies with an annular conical supporting surface on the conical shoulder surface 18 of the support. The cap has fixing means 2365, namely latching means 2365, which, for example, are similarly designed to the fixing or latching means 65 of the impression element 50. The fixing or latching means 2365 are latched into the annular groove 24 of the support and detachably connect the cap 2360 to the support. Additionally, if necessary, the cap can also be attached to the support with an occlusal screw 2370 and, for example, be designed for multi or uni-positioning. A superstructure 2375 is built onto the cap.

The versions of the supports and impression elements described using FIGS. 5 through 42 can be similarly designed, as long as each time nothing was written to the contrary, to the supports and impression elements described using FIGS. 1 to 4 and/or using other preceding figures. In addition, features from the different versions shown can be combined with each other.

The devices can also be changed in various ways. With the support 3 seen in FIGS. 1 to 4, one can design the support's 3 positioning projections 25 and the annular groove 24 dividing these from the from the support's shoulder such that the undercut serving to clip on the impression element is completely divided by the support's positioning recesses into several parts distributed along the circumference of the support, which then could possibly be seen as several undercuts.

The fixing sections, seen in FIGS. 34, 35, 38, 39, 40 41 and protruding into a support's hole, of the fixing means of an element connected to the support can, for example, additionally be subdivided by axial incisions into springable tongues or such. The fixing sections which engage with the interior threading of a support can possibly be provided with small, barb-shaped latch projections or noses. During connection to the implant, these can more or less be latched into the helical groove of the interior threading.

The supports, comprising a one-piece implant, can be replaced by an implant and a separate secondary part which forms the support's head and is detachably screwed into the interior threading of a pocket hole of the implant. The secondary part can then itself have a pocket hole with an interior threading.

Finally, reference is made to U.S. patent application Ser. No. 09/424,515 of the same applicant, submitted claiming the priorities of Swiss patent applications 1218/97 and 1221/97, the content of which is hereby incorporated in this patent application, insofar as there are no contradictions.

What is claimed is:

1. A device for forming a dental prosthesis, comprising:

a support, and an element detachably connected to the support by fixing means, wherein the support has an anchoring part designed for anchoring in at least one of a bone and a master model, a head designed to protrude from the at least one of the bone and the master model, and a shoulder located between the head and the anchoring part, wherein the element has a wall which surrounds an interior space in a cross-section and has an annular supporting surface, wherein, when the device is assembled, the support surface lies on the shoulder and the element surrounds the head in said cross section, wherein at least one of the fixing means and the support has at least one elastically deformable section, wherein, when the device is assembled, the fixing means are at least one of jammed and latched with the support either externally on the support on a side of the shoulder facing away from the anchoring part or in an axial hole of the support, and wherein the at least one elastically deformable section is located in the interior space and separated from the wall by a space.

2. The device in accordance with claim 1, wherein the anchoring part defines an axis, wherein the shoulder has an annular shoulder surface, wherein the shoulder surface and the supporting surface are both conical or both flat, have outer edges, and lie on each other when the device is assembled, and wherein the outer edges are visible when the device is assembled from its surroundings along their entire circumferences in viewing directions which are approximately radial to the axis of the anchoring part.

3. The device in accordance with claim 1 wherein the head defines an axis, and wherein the fixing means are bendable such that the element is at least one of removable from the support and attachable to the support by displacement in a direction which is allowed to form an angle with an axis of the head up to at least approximately 15°.

4. The device in accordance with claim 1, wherein said elastically deformable section is elastically bendable.

5. The device in accordance with claim 1, wherein the shoulder is coaxial to an axis of the anchoring part which is defined by the anchoring part and wherein the head has a head section which is essentially parallel to said axis of the anchoring part and a generally conical head section which tapers away from said head section to a free end of the head.

6. The device in accordance with claim 5, wherein the shoulder defines an annular, conical shoulder surface, wherein the conical head section defines a conical surface which forms a smaller angle with the axis of the anchoring part than does the shoulder surface, wherein the supporting surface lies on the conical shoulder surface without a gap, and wherein the element has a conical interior surface which is supported by the generally conical head section with little play.

7. The device in accordance with claim 6, wherein the conical shoulder surface tapers toward the head and forms, with the axis of the anchoring part, an angle between 40° and 50°, wherein the generally conical head section defines a conical surface forming, with the axis of the anchoring part, an angle between 15° and 25°, and wherein the element and the elastically deformable section are configured such that the element is at least one of removable from the support and attachable to the support by displacing the element in a direction which can either be parallel to the axis of the anchoring part or form with said axis an angle of at least 15°.

8. The device in accordance with claim 1, wherein the head has at least one recess which is positioned such that it can receive a projection of the element and thus ensure that the element does not turn.

9. The device in accordance with claim 1, wherein the support defines an axis, wherein the head has recesses distributed around the axis, and wherein said recesses include several first recesses with identical shapes and measurements and a second recess that is at least one of wider and deeper than the first recesses.

10. The device in accordance with claim 1, wherein the support has at least one of an undercut and an annular groove, and wherein the fixing means can be latched behind the undercut or in the annular groove and are designed such that the fixing means, when in a latched state, produce a force which presses the element against the shoulder.

11. The device in accordance with claim 1, wherein the fixing means engage with an interior threading in the hole of the support when the device is assembled.

12. The device in accordance with claim 1, wherein the fixing means have one of an annular nose and noses distributed along a circle, and wherein, when the device is assembled, each nose points inwards or outwards in an approximately radial direction to a fixing section of the support and engages with said fixing section.

13. The device in accordance with claim 1, wherein a section of the element which lies on the shoulder when the device is assembled and the fixing means are formed from a one-piece body or from bodies which were originally separate but are rigidly attached to each other.

14. The device in accordance with claim 1, wherein the anchoring part defines an axis, wherein the element and the fixing means comprise separate bodies which can be displaced along the axis with respect to one another, wherein the element has a fixing surface which faces away from the support and forms an angle with the axis, and wherein the fixing means engage with the fixing surface.

15. The device in accordance with claim 14, wherein the fixing means engage with the fixing surface using elastically deformable pressing means that produce a force which presses the element against the shoulder, wherein the pressing means have either an annular lip which surrounds the axis or a wreath of lips distributed along the axis and comprise, together with the fixing section, a one-piece body made of synthetic material.

16. The device in accordance with claim 1, wherein the anchoring part, the shoulder, and the head are rigidly and undetachably connected to each other and have a one-piece body which extends from a free end of the anchoring part to a free end of the head.

17. The device in accordance with claim 1, wherein the support has an implant and an originally separate secondary part, wherein the implant forms the anchoring part and has an end which forms the shoulder as well as an axial hole, wherein the secondary part is attached on the implant in the hole of the implant and has a section which protrudes from the implant and forms the head, and wherein the fixing means are at least one of jammed and latched with the secondary part when the device is assembled.

18. The device in accordance with claim 1, wherein the element which can be detachably connected to the support is an impression element.

19. The device in accordance with claim 1, wherein said wall is rigid and surrounds said interior space to the supporting surface along its entire circumference continuously.

20. A device for forming a dental prosthesis comprising:
a support, and
an impression element detachably connectable to the support,
wherein the support has an anchoring part designed for anchoring in at least one of a bone and a master model, a head designed to protrude from said at least one of the bone and the master model,
wherein an annular shoulder surface is located between the anchoring part and the head and an annular groove is located between the shoulder surface and a free end of the head,
wherein the impression element has a wall which surrounds an interior space in a cross-section and has an annular supporting surface,
wherein the wall, when the device is assembled, surrounds the head and lies with the supporting surface continuously along the entire circumference of the shoulder surface,
wherein the impression element further includes a fixing means with at least one elastically deformable and bendable section,
wherein the at least one elastically deformable section is located within said interior space and separated from the wall by a hollow portion of the interior space, and
wherein, when the device is assembled, the fixing means projects into the annular groove and is latched with the support.

21. The device in accordance with claim 20, wherein the shoulder surface and the supporting surface are each flat or conical, wherein the anchoring part and the head define a common axis, wherein the head has a first head section which is essentially parallel to the common axis and a second, generally conical head section which tapers away from the first head section to a free end of the head, and wherein the second head section defines a conical surface which forms a smaller angle with the axis than does the shoulder surface.

22. The device in accordance with claim 21, wherein the conical surface defined by the second, generally conical head section forms, with the axis, an angle from 10° to 30°.

23. The device in accordance with claim 21, wherein the conical surface defined by the second, generally conical head section forms, with the axis, an angle from 15° to 25°, and wherein the fixing means is bendable such that the impression element is at least one of removable from the support and attachable to the support by displacing the impression element in a direction which either is parallel to the axis or forms an angle with the axis up to at least approximately 15°.

24. The device in accordance with claim 23, wherein the shoulder surface is conical and forms, with the axis, an angle from 40° to 50°.

25. The device in accordance with claim 21, wherein the supporting surface, when the device is assembled, lies on the shoulder surface without a gap, and wherein the impression element has a conical interior surface which is supported by the generally conical head section with little play.

26. The device in accordance with claim 20, wherein the wall of the impression element is rigid.

27. A device for forming a dental prosthesis comprising:
   a support, and
   an impression element detachably connectable to the support,
   wherein the support has an anchoring part designed for anchoring in at least one of a bone and a master model and a head designed to protrude from said at least one of the bone and the master model,
   wherein an annular shoulder surface is located between the anchoring part and the head and an annular groove is located between the shoulder surface and a free end of the head,
   wherein the impression element has a wall which surrounds an interior space in a cross-section and has an annular supporting surface,
   wherein the wall, when the device is assembled, surrounds the head and lies with the supporting surface continuously along the entire circumference of the shoulder surface,
   wherein the impression element further has a fixing means with at least one elastically deformable and bendable section,
   wherein the at least one elastically deformable section is located within said interior space and separated from the wall by a hollow portion of the interior space,
   wherein, when the device is assembled, the fixing means projects into the annular groove and is latched with the support,
   wherein the shoulder surface and the supporting surface are both conical,
   wherein the anchoring part and the head define a common axis,
   wherein the head has a first head section which is essentially parallel to the common axis and a second, generally conical head section which tapers away from the first head section to a free end of the head,
   wherein the second head section defines a conical surface which forms a smaller angle with the axis than does the shoulder surface,
   wherein the conical surface defined by the second, generally conical head section forms, with the axis, an angle from 15° to 25°, and
   wherein the fixing means is bendable such that the impression element is at least one of removable from the support and attachable to the support by displacing the impression element in a direction which either is parallel to the axis or forms an angle with the axis up to at least approximately 15°.

28. The device in accordance with claim 27, wherein the supporting surface, when the device is assembled, lies on the shoulder surface without a gap, and wherein the impression element has a conical interior surface which is supported by the generally conical head section with little play.

* * * * *